US008868357B2

(12) United States Patent
Huitt et al.

(10) Patent No.: US 8,868,357 B2
(45) Date of Patent: *Oct. 21, 2014

(54) TEMPERATURE COMPENSATION FOR PNEUMATIC PUMPING SYSTEM

(75) Inventors: Bruce E. Huitt, Odessa, FL (US);
Douglas E. Vincent, Pelham, NH (US);
Gideon Hecht, Seminole, FL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 760 days.

This patent is subject to a terminal disclaimer.

(21) Appl. No.: 13/110,357

(22) Filed: May 18, 2011

(65) Prior Publication Data

US 2011/0218486 A1 Sep. 8, 2011

Related U.S. Application Data

(63) Continuation of application No. 11/773,525, filed on Jul. 5, 2007, now Pat. No. 7,957,927.

(51) Int. Cl.
*G01F 15/02* (2006.01)
*A61M 1/28* (2006.01)
*G06F 17/40* (2006.01)
*G06F 19/00* (2011.01)

(52) U.S. Cl.
CPC ............... *A61M 1/28* (2013.01); *G06F 17/40* (2013.01); *G06F 19/00* (2013.01); *G01F 15/02* (2013.01); *A61M 2205/12* (2013.01); *A61M 2205/3372* (2013.01); *A61M 2205/3396* (2013.01)
USPC ............... 702/42; 73/1.16; 73/861.01; 702/1; 702/100; 702/127; 702/187; 702/189

(58) Field of Classification Search
CPC ........... A61M 1/00; A61M 1/14; A61M 1/16; A61M 1/28; A61M 2205/00; A61M 2205/12; A61M 2205/123; A61M 2205/125; A61M 2205/127; A61M 2205/33; A61M 2205/3368; A61M 2205/3372; A61M 2205/3379; A61M 2205/3396; G01D 7/00; G01D 9/00; G01D 21/00; G01F 3/00; G01F 15/00; G01F 15/02; G01F 25/00; G06F 11/00; G06F 11/30; G06F 11/32; G06F 11/34; G06F 17/00; G06F 17/40; G06F 19/00
USPC ............... 73/1.01, 1.16, 1.19, 1.21, 149, 198, 73/199, 861, 861.01, 865.8; 222/1, 14, 23, 222/36, 52, 54, 55, 71, 146.1, 146.2, 192; 604/19, 27, 29; 702/1, 33, 45, 47, 50, 702/55, 85, 100, 127, 187, 189
See application file for complete search history.

(56) References Cited

U.S. PATENT DOCUMENTS 3,173,003 A 3/1965 Muller-Girard
3,302,451 A 2/1967 Martin
(Continued)

FOREIGN PATENT DOCUMENTS

WO 94/20158 9/1994
WO 97/02893 1/1997
(Continued)

OTHER PUBLICATIONS
International Search Report and Written Opinion for International Application No. PCT/US2008/068948 mailed on May 14, 2009.
(Continued)

*Primary Examiner* — Edward Cosimano
(74) *Attorney, Agent, or Firm* — K&L Gates LLP

(57) ABSTRACT

Temperature compensation is applied to correct for temperature mismatch between a reference chamber and a disposable chamber in a pneumatic pumping system for dialysis fluid for peritoneal dialysis. The mismatch creates an error in the calculation of pumping volume of dialysate fluid. Applying a correction for the temperature mismatch helps to more precisely control the volume of dialysate that is metered to the patient. Also disclosed are ways to keep temperatures constant and to use temperature sensors to accurately measure the temperatures of the chambers. In other aspects, the temperature of the dialysate fluid itself may be measured and used to apply a correction to the volume of fluid that is pumped to the patient.

25 Claims, 16 Drawing Sheets

(56) References Cited

U.S. PATENT DOCUMENTS

| | | |
|---|---|---|
| 3,538,766 A | 11/1970 | Kugler |
| 3,905,229 A | 9/1975 | Togo et al. |
| 3,969,939 A | 7/1976 | Grzeslo |
| 4,101,056 A | 7/1978 | Mattimoe et al. |
| 4,674,316 A | 6/1987 | Albrecht et al. |
| 4,720,800 A | 1/1988 | Suzuki et al. |
| 4,826,482 A | 5/1989 | Kamen |
| 4,829,449 A | 5/1989 | Polesnak et al. |
| 4,956,996 A | 9/1990 | Morris |
| 5,050,094 A | 9/1991 | Kitano |
| 5,062,774 A | 11/1991 | Kramer et al. |
| 5,350,357 A | 9/1994 | Kamen et al. |
| 5,431,626 A | 7/1995 | Bryant et al. |
| 5,474,683 A | 12/1995 | Bryant et al. |
| 5,628,908 A | 5/1997 | Kamen et al. |
| 5,634,896 A | 6/1997 | Bryant et al. |
| 5,895,838 A | 4/1999 | Harjunmaa et al. |
| 5,944,048 A | 8/1999 | Bump et al. |
| 5,975,126 A | 11/1999 | Bump et al. |
| 5,989,423 A | 11/1999 | Kamen et al. |
| 6,595,944 B2 | 7/2003 | Balschat et al. |
| 8,715,235 B2 * | 5/2014 | Childers et al. ............... 604/131 |
| 2005/0251086 A1 | 11/2005 | Sternby |
| 2007/0007208 A1 | 1/2007 | Brugger et al. |
| 2009/0012461 A1 | 1/2009 | Childers et al. |

FOREIGN PATENT DOCUMENTS

| | | |
|---|---|---|
| WO | 2004/062710 | 7/2004 |
| WO | 2005/107833 | 11/2005 |

OTHER PUBLICATIONS

Mexican Office Action issued Apr. 12, 2013 for related Mexican Appln. No. MX/a/2010/000274.

\* cited by examiner

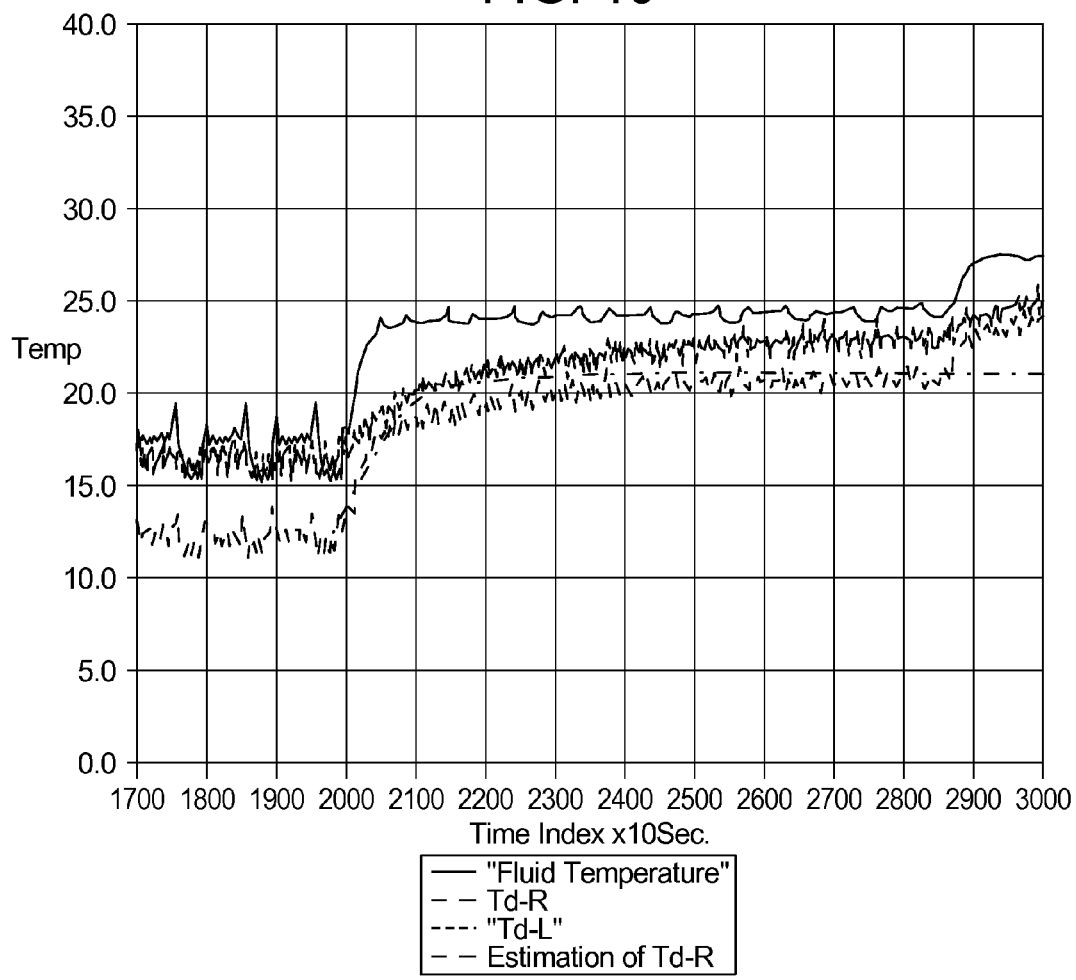
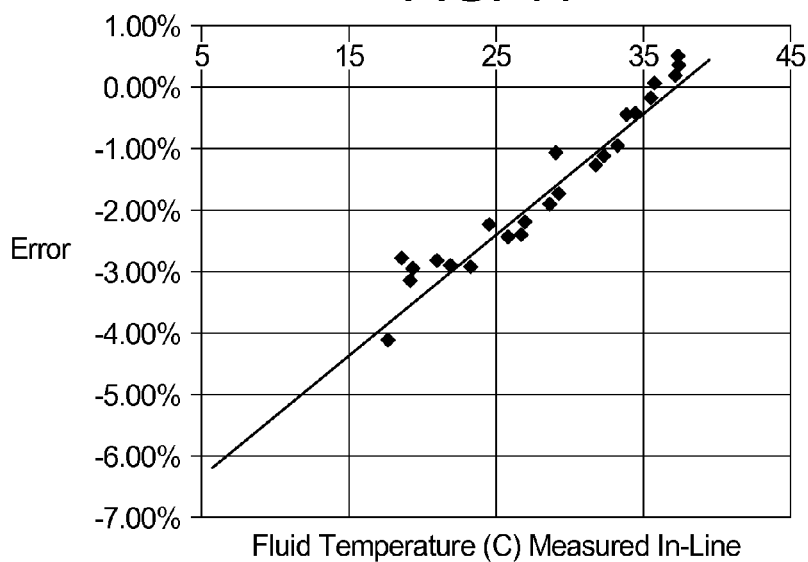

TEMPERATURE COMPENSATION FOR PNEUMATIC PUMPING SYSTEM

PRIORITY

This application claims priority to and the benefit as a continuation application of U.S. patent application entitled, "Temperature Compensation For Pneumatic Pumping System", Ser. No. 11/773,525, filed Jul. 5, 2007, now U.S. Pat. No. 7,957,927, the entire contents of which are incorporated herein by reference and relied upon.

BACKGROUND

The field is that of medical instruments, pneumatic pumping of small, precise volumes in medical instruments, and temperature compensation for medical instruments and precise fluid movements.

Pneumatic pumping systems are used to pump many fluids, including fluids with medical applications. One such application is a fluid management system used to pump dialysate fluid for an automated peritoneal dialysis system. In general terms, persons whose kidneys do not function adequately may use the peritoneal membrane instead. Diffusion and osmotic exchanges take place across the peritoneal membrane between the dialysis solution and the bloodstream. These exchanges remove the waste products normally excreted by the kidneys. The waste products typically include sodium and chloride ions, and other compounds normally excreted through the kidneys, such as urea, creatinine, and water.

In a typical treatment, dialysis fluid enters the patient, dwells for a period of time, usually several hours, and is then removed. The cycle may be repeated as often as the attending physician believes is necessary. Peritoneal Dialysis (PD) may be used in the form of continuous ambulatory peritoneal dialysis (CAPD), in which a patient performs a PD cycle about four times a day, using a cycle of infusing the peritoneal dialysis fluid, dwell for a period of time, and then draining the PD fluid. Each cycle lasts for several hours. In automated peritoneal dialysis (APD), a cycler performs the drain, fill and dwell tasks while the patient sleeps at night. There are also a number of other recognized treatment regimes, such as intermittent PD ("IPD") or continuous cycling PD ("CCPD"), in which the cycle is performed about 6 times per day and the peritoneal cavity is completely drained during the drain portions of the cycle.

Regardless of the particular regimen used, peritoneal dialysis is a difficult procedure for patients. In order to preserve patient comfort, and thus to encourage the patient to return for treatment, it is important to accurately control the volume of dialysate that is pumped into the patient. The volume of dialysis fluid is important for several reasons. Excess volume by itself could cause patient discomfort or injury, while too little volume will result in a longer and less-effective change therapy. The difference in temperature between the pneumatic pumping system at ambient temperature and the temperature at which it was calibrated (at the factory) detracts from the accuracy of the volume of the dialysate pumped to the patient. What is needed is a better way to compensate for the difference in these temperatures.

SUMMARY

A first embodiment is a method of compensating for temperature error in a pneumatic pumping system of a peritoneal dialysis system, the peritoneal dialysis system including a pumping mechanism with a disposable cassette and at least one disposable chamber, wherein fluid communication is established between the peritoneal dialysis system and a peritoneal cavity of a patient. The method includes calculating a corrected volume of air in a disposable chamber, $$V_d = V_r * \frac{(Pr_2 - Pr_1)}{(Pd_1 - Pd_2)}$$

wherein $V_d$ is the corrected volume, $V_r$ is a reference volume of the chamber, $(Pr_2-Pr_1)$ is a pressure difference between a high pressure in the reference chamber and a pressure in the reference chamber after equalization, $(Pd_1-Pd_2)$ is a pressure difference between a high pressure in the disposable chamber and a pressure in the delivery chamber after equalization, wherein pressures after equalization comprise pressure measurements after the delivery and reference chambers are connected. The method also includes multiplying the result by a ratio of a temperature in the disposable chamber to a temperature in the reference chamber $T_d/T_r$, and multiplying the result by a ratio of $Tr_{cal}/Td_{cal}$, wherein $Tr_{cal}$ is a temperature in the reference chamber during a calibration procedure and $Td_{cal}$ is a temperature in the disposable chamber during the calibration procedure, wherein the temperature during a calibration procedure is constant in the reference and disposable volumes. The method then includes calculating a corrected volume of air delivered by the disposable chamber of the system by applying the correction factor, and correcting a volume of dialysate pumped by the dialysis system using the corrected volume of air.

Another embodiment is a method of compensating for temperature error in a dialysis system, the dialysis system including a pumping mechanism with a disposable cassette and at least two disposable chambers, wherein fluid communication is established between the peritoneal dialysis system and a peritoneal cavity of a patient. The method includes measuring a temperature of a particular pumping chamber, selecting an offset temperature, said offset temperature dependent on the temperature and on the particular pumping chamber, applying the offset temperature to the measured temperature of the particular pumping chamber, and correcting a volume of air pumped by the particular pumping chamber using the formula $$V_d = \frac{V_r * T_{do} * Tr_{cal} * (Pr_2 - Pr_1)}{T_r * Td_{cal} * (Pd_1 - Pd_2)}$$

wherein $V_d$ is the corrected volume, $V_r$ is the nominal chamber volume, $T_{do}$ is the temperature of the chamber with the offset applied, $T_r$ is the temperature of the reference chamber of the dialysis system, $Tr_{cal}/Td_{cal}$ is a factory correction factor calibrated at 37 C, and $(Pr_2-Pr_1)/(Pd_1-Pd_2)$ is a ratio of the pressure differences of the reference chamber and a pumping chamber before and after equalization.

Another embodiment is a method of compensating for temperature error in a pneumatic pumping system of a peritoneal dialysis system, the peritoneal dialysis system including a pumping mechanism with a membrane and a disposable cassette and at least one disposable chamber, wherein fluid communication is established between the peritoneal dialysis system and a peritoneal cavity of a patient. The method includes calculating a corrected volume of air in a disposable chamber, $$V_d = V_r * \frac{(Pr_2 - Pr_1)}{(Pd_1 - Pd_2)}$$

wherein $V_d$ is the corrected volume, $V_r$ is a reference volume of the chamber, and $(Pr_2-Pr_1)$ is a pressure difference between a high pressure in the reference chamber and a pressure in the reference chamber after equalization, and $(Pd_1-Pd_2)$ is a pressure difference between a high pressure in the disposable chamber and a pressure in the delivery chamber after equalization, wherein pressures after equalization comprise pressure measurements after the delivery and reference chambers are connected. The method also includes multiplying the result by a ratio of a temperature of a membrane adjacent the disposable chamber to a temperature in the reference chamber, $T_m/T_r$, multiplying the result by a ratio of $Tr_{cal}/Td_{cal}$, wherein $Tr_{cal}$ is a temperature in the reference chamber during a calibration procedure and $Td_{cal}$ is a temperature in the disposable chamber during the calibration procedure, wherein the temperature during a calibration procedure is constant in the reference and disposable volumes. The method also includes calculating a corrected volume of air delivered by the disposable chamber of the system by applying the correction factor, and correcting a volume of dialysate pumped by the dialysis system using the corrected volume of air.

Another embodiment is method of compensating for temperature error in a pneumatic pumping system of a peritoneal dialysis system, the peritoneal dialysis system including a pumping mechanism with a membrane and a disposable cassette and at least one disposable chamber, wherein fluid communication is established between the peritoneal dialysis system and a peritoneal cavity of a patient. The method includes measuring a temperature of air pumped from a disposable chamber, and calculating a corrected volume of air in the disposable chamber, $$V_d = V_r * \frac{(Pr_2 - Pr_1)}{(Pd_1 - Pd_2)}$$

wherein $V_d$ is the corrected volume, $V_r$ is a reference volume of the chamber, and $(Pr_2-Pr_1)$ is a pressure difference between a high pressure in the reference chamber and a pressure in the reference chamber after equalization, and $(Pd_1-Pd_2)$ is a pressure difference between a high pressure in the disposable chamber and a pressure in the delivery chamber after equalization, wherein pressures after equalization comprise pressure measurements after the delivery and reference chambers are connected. The method also includes multiplying the result by a ratio of an offset temperature to a temperature in the reference chamber, $T_m/T_r$, the offset temperature comprising the measured temperature of the air corrected by an offset and wherein the offset depends on the measured temperature and the disposable chamber, and multiplying the result by a ratio of $Tr_{cal}/Td_{cal}$, wherein $Tr_{cal}$ is a temperature in the reference chamber during a calibration procedure and $Td_{cal}$ is a temperature in the disposable chamber during the calibration procedure, wherein the temperature during a calibration procedure is constant in the reference and disposable volumes. The method then includes calculating a corrected volume of air delivered by the disposable chamber of the system by applying the correction factor and then correcting a volume of dialysate pumped by the dialysis system using the corrected volume of air.

Another embodiment is a method of controlling pneumatic air temperature in a dialysis system. The method includes mounting a first strip heater in a pneumatic distribution manifold, the pneumatic distribution manifold further comprising a precision reference volume, controlling a temperature of the first strip heater by monitoring a temperature of the manifold, sensing a temperature of air in a disposable chamber, calculating a corrected volume of air delivered by the disposable chamber, and correcting a volume of dialysate pumped by the dialysis system using the corrected volume of air.

Additional embodiments, features and advantages are described herein, and will be apparent from, the following Detailed Description and the figures.

BRIEF DESCRIPTION OF THE FIGURES

FIG. 10 depicts the time lag and temperature differences along with an estimate of the temperature of one of the pistons;

FIG. 11 depicts the volumetric error based on a first method of applying a steady-state temperature offset for a pneumatic pumping system.

DETAILED DESCRIPTION

In pneumatic pumping systems, a given volume of air from a pumping or dispensing chamber is used to displace a volume of liquid (dialysate) that is dispensed to a patient. In general terms, the volume of liquid dialysate dispensed to the patient is controlled by controlling the amount of air dispensed from the pumping chamber or chambers. The amount of air is calculated using the well known gas law, and then corrected for the temperature and pressure of the air. The "volume" of air provided by the pumping chamber is clearly a misnomer, since the known volume of a pumping chamber can hold vastly differing quantities of air, depending on the temperature and the pressure of the air. Assuming that air is a perfect gas precisely obeying the gas law, what is really sought is the number of gas molecules in the volume, corrected for temperature and pressure. Nevertheless, the volume of the chamber is relatively constant, within the limits of ambient temperature excursions and the thermal expansion of the material used for the chamber walls. We can therefore use chamber volume or gas volume as a substitute for the calculating the number of molecules and then converting the number of molecules to a volume on the dialysis machine or disposable, that volume corresponding conveniently to the volume of dialysate. That substitution is well known to those having skill in the art, and that substitution is used in this patent for temperature compensation in a pneumatic pumping system. In addition, all temperatures used for temperature correction factors refer to absolute temperatures, e.g., in degrees Kelvin or Rankine.

Figure 1A:
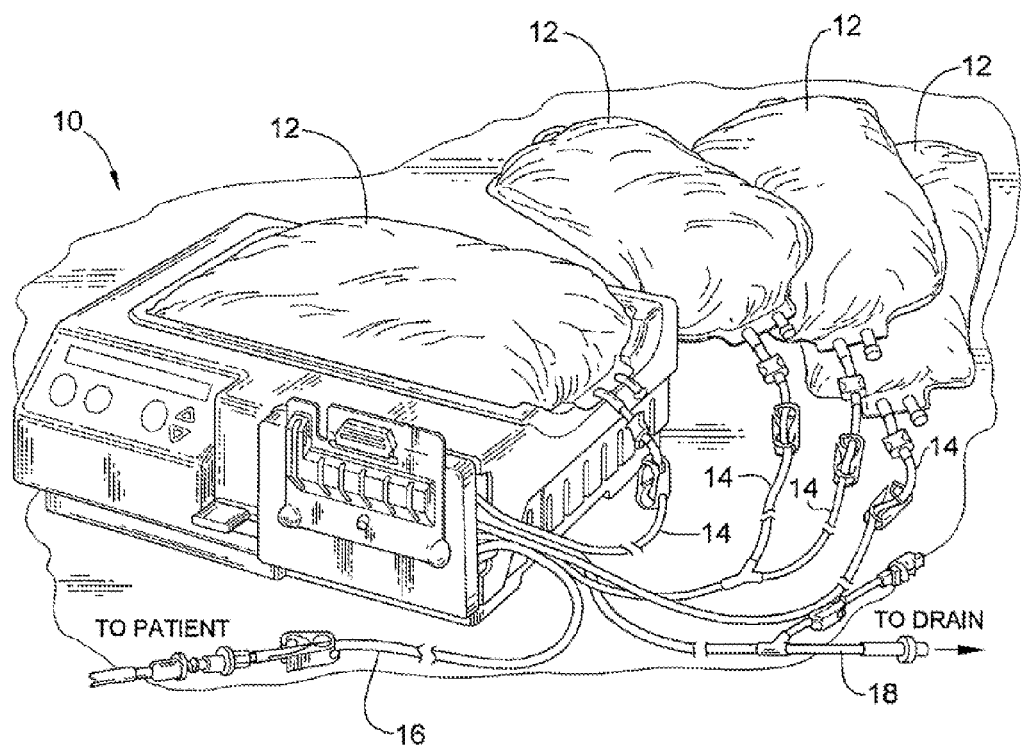
FIGS. 1A, 1B and 1C depict systems for peritoneal dialysis.

In one embodiment, a testing mechanism for testing a medical fluid is incorporated with a medication delivery system such as a dialysis machine 10, illustrated in FIG. 1A. In another embodiment, a testing mechanism for testing a medical fluid is incorporated within a different medication delivery system such as an infusion pump (not shown). The testing mechanisms of the present disclosure are illustrated and described as cooperating with a dialysis machine, but it should be understood by one skilled in the art that the dialysis machine is an exemplary medication delivery system and the testing mechanism can be used in cooperation with any medication delivery system that delivers a medical fluid to a patient. It should be understood by one skilled in the art that the testing mechanisms of the present disclosure can be incorporated within a medication delivery system, or the testing mechanisms of the present disclosure can be formed as devices separate from the medication delivery system, but which maintain an operative connection to the medication delivery system. A medical delivery system for a particular medical fluid may include a bag or container in which the medical fluid is typically or commercially furnished, and may include integral or appended tubing for delivery to the patient.

A plurality of medication containers 12 containing medical fluid are attached to the dialysis machine 10, as shown in FIG. 1A. In an embodiment, each medication container 12 contains the same medical fluid. For example, each medication container 12 contains a dialysis solution, or dialysate, containing glucose molecules. In another embodiment, each medication container 12 includes different medical fluids that are combinable within the dialysis machine 10 prior to being delivered to a patient. A disposable line set 14 operatively connects each medication container 12 to the dialysis machine 10. A line 16 leading to the patient, formed of a disposable tube, delivers the medical fluid from the dialysis machine 10 to the patient (not shown). A drain line 18 formed of a disposable tube directs spent dialysate and blood waste products from the dialysis machine 10 to a drain container (not shown).

Figure 1B:
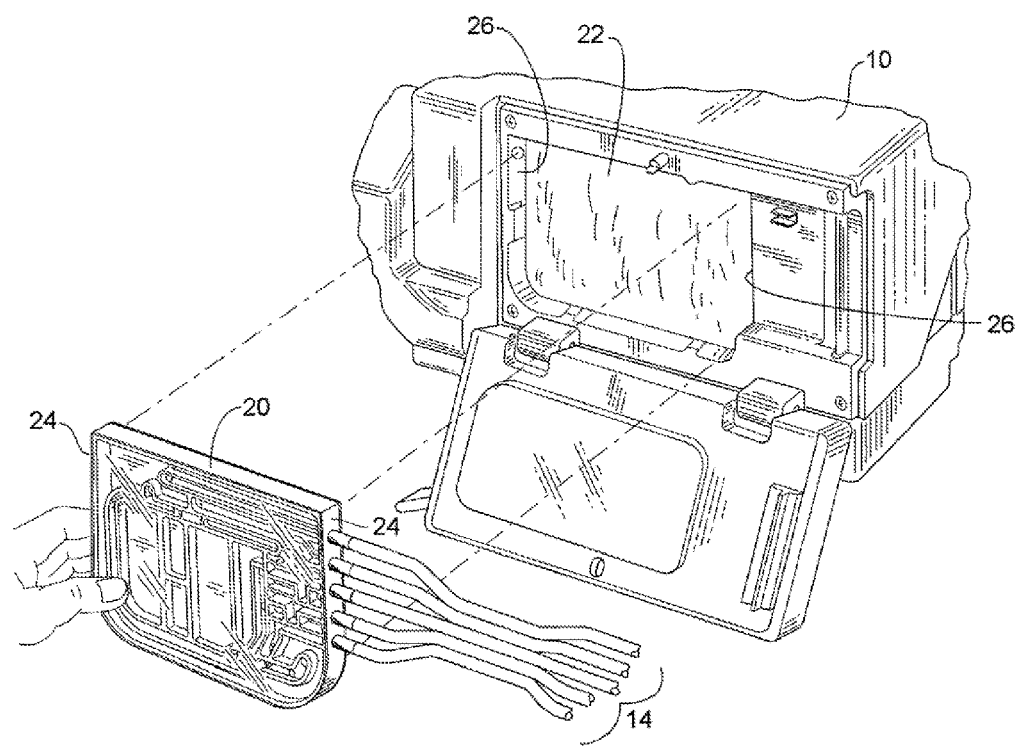
Figure 1C:
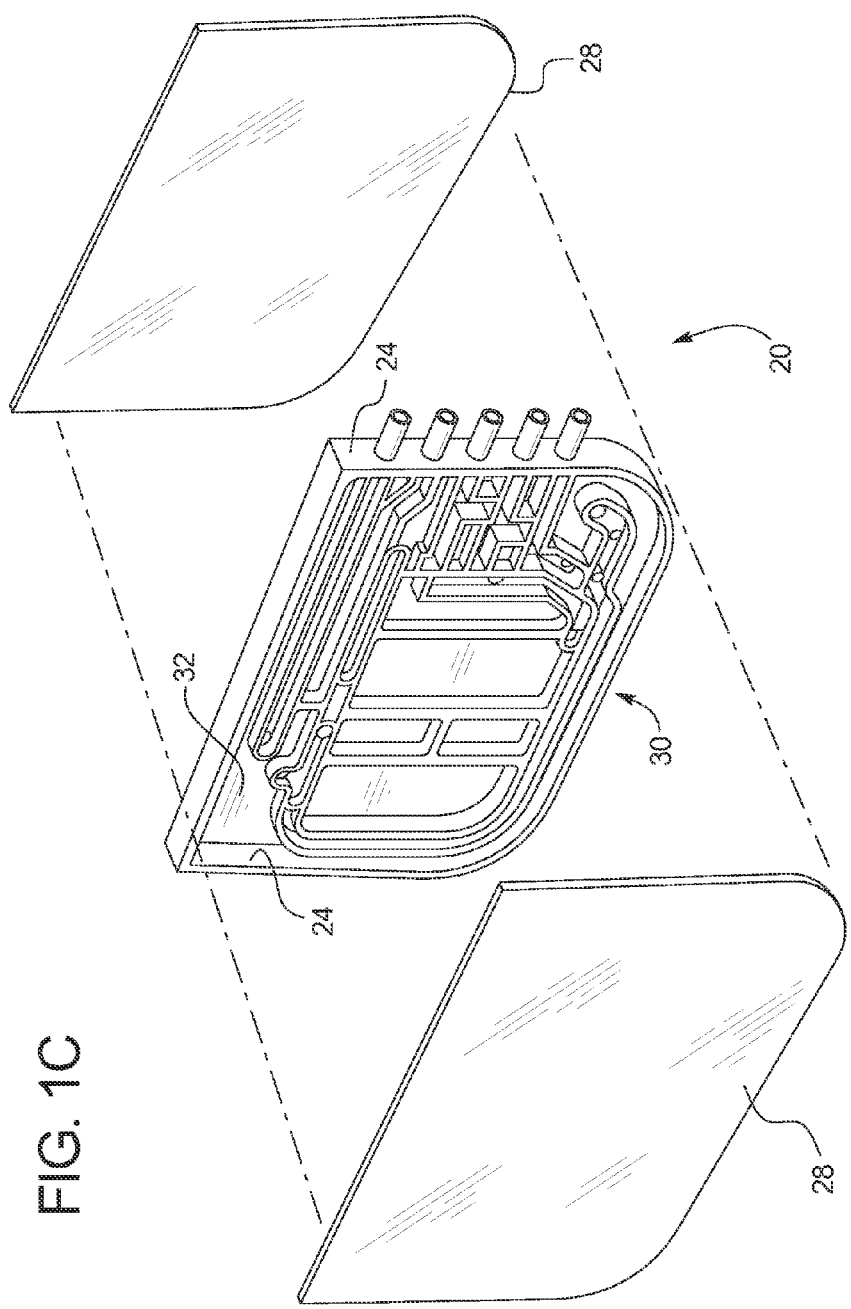

The dialysis machine 10 receives a disposable fluid containment device, such as a cassette 20 or a portion of the line set 14, to which the medication containers 12 are connected, as illustrated in FIG. 1B. The dialysis machine 10 includes a recessed area 22 for receiving the disposable cassette 20. The recessed area 22 is sized and shaped to provide a snug fit with the disposable cassette 20 to ensure the cassette 20 is properly aligned within the recessed area 22. In particular, the opposing side walls 24 of the cassette 20 fit snuggly within opposing inner walls 26 of the recessed area 22. As shown in FIG. 1C, the cassette 20 includes a pair of flexible membranes 28 attached to opposing surfaces of a rigid structure 30. The flexible membranes 28 are operatively attached to the rigid structure 30 to provide, for example, pumping movement to allow the medical fluid received from the medication containers 12 and delivered to the patient.

Figure 2:
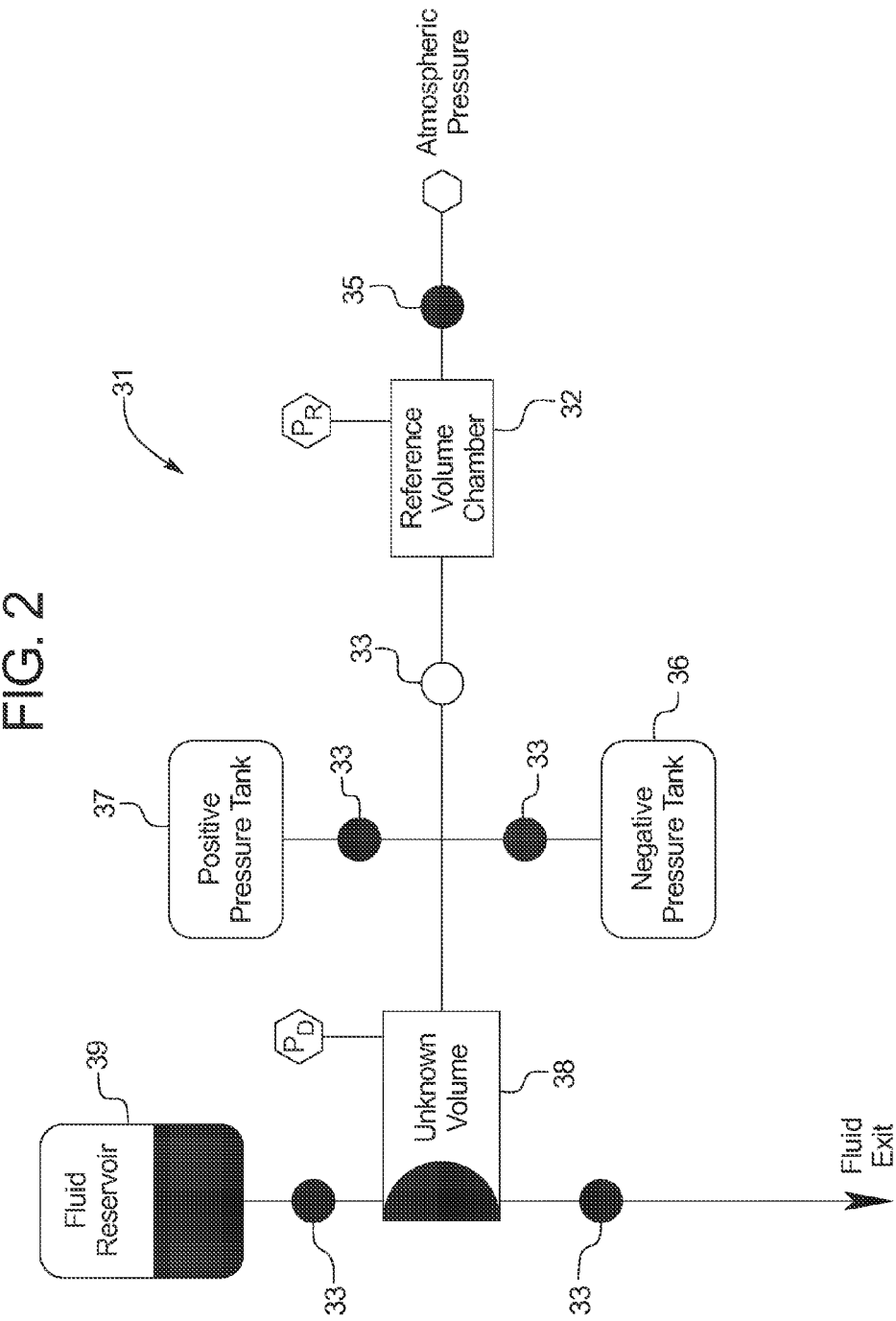
FIG. 2 depicts a pumping system for dialysis fluid.

Pumping of dialysate fluid can be described with respect to the prior art fluid pumping system 31 depicted in FIG. 2. A preferably two-headed pump or compressor (not shown) is connected with a series of valves 33 to a reference volume chamber 32, which is also connected via valve 35 to the atmosphere and to a reference pressure gauge Pr. Using one head, the pump provides a source of pressurized air, typically about 4-5 psig, to a positive pressure tank 37. Using the vacuum head, the pump can also act as a source of air at a lower pressure for the "negative" pressure tank 36. The "negative" pressure tank typically has a pressure less than atmospheric by about 4-5 psi, that is, at about 9-10 psia. In order to pump dialysate fluid, the pumping chamber 38, with membrane 28, which is equipped with a pressure gauge Pd, is filled with an unknown amount of dialysate fluid from a fluid reservoir 39. An amount of air is measured in the reference volume chamber 32 and is then pumped into the pumping chamber 38, with the appropriate valves opened or closed as is necessary.

Thermal Compensation

Air at one temperature flows from the reference volume chamber 32 into the air or right side of disposable chamber 38, which may be at a second temperature. When the air flows in, dialysate on the opposite side of the membrane 28 may be at yet another temperature, and the dialysate is pushed to the fluid outlet, i.e., to tubing that leads to the patient. After this cycle, the pumping or dispensing chamber is then filled as fluid from the fluid inlet flows into the pumping or dispensing chamber. The fluid may be at yet another temperature. The thermal energy flow through the membrane causes a temperature difference between pumping chamber 38 and reference chamber 32.

There are many ways to compensate for the temperature differences in these systems. One way used to estimate the volume of air in the dispensing chamber, $V_d$, is to use simple pressure correction of the form $$V_d = V_r (Pr_2 - Pr_1)/(Pd_1 - Pd_2) \qquad \text{(Equation 1)}$$

where $Pr_1$ and $Pr_2$ are the pressures measured in the reference chamber at atmospheric pressure and after equalization respectively with the pressurized dispensing chamber at a high pressure. $Pd_1$ and $Pd_2$ are the pressures measured in the dispensing chamber at high pressure and after the two chambers are equalized. $V_r$ is the reference chamber volume as calibrated at the factory. The calculation provides a measure of the air volume in the dispensing chamber. Calculating the volume differences in air volume of the dispensing chamber prior to and after the movement of fluid allows the calculation of the displaced fluid. As noted, however, this calculation does not account for the error caused by temperature difference.

One improvement therefore uses measurement of temperature in both the dispensing chamber, also known as the piston area, and the volume reference chamber to make a correction to the air volume calculation. A thermocouple or thermistor is preferably placed in an area of the dispensing chamber or piston where it will readily detect the temperature of the air. In one embodiment, the temperature-measuring device is placed within the chamber, in physical contact with the walls of the piston chamber, which is filled with a foamed material to minimize thermodynamic effects. This contact enables the temperature measuring device to more accurately measure the air temperature, because the air quickly equilibrates with its surroundings, the material in the dispensing chamber or piston, due to its low thermal mass. In the same manner, a thermocouple may be placed in the reference chamber to complete the data necessary for a more accurate calculation. The thermocouple in the reference chamber is preferably also placed in contact with the walls of the chamber.

Using these temperatures, a correction factor of the temperature of the dispensing chamber or piston, $T_d$, divided by the temperature of the reference chamber, $T_r$, may be used. In addition, it has been discovered that the correction is improved by using an additional correction factor, when pneumatic piston air temperatures are not at the temperatures used to calibrate the system. The calibration is preferably accomplished at a manufacturing facility or other convenient facility, and is accomplished using fluids at body temperature, i.e., 37C. The additional factor is the temperature in the reference chamber divided by the temperature in the dispensing chamber or piston, i.e., $Tr_{cal}/Td_{cal}$. This correction factor may be stored in a memory of the dialysis machine controller or in the dialysis controller (e.g., memory 46 or 56 shown in FIGS. 3 and 4). In most instances, the air used to pump fluid will be cooler than body temperature, and therefore will have a lower volume than air (and dialysate fluid) at body temperature. In most instances, then, the error will be negative, i.e., a lower amount of fluid will be pumped than is needed by the patient.

The correction factor is thus $$V_d = \frac{V_r * T_d * Tr_{cal} * (Pr_2 - Pr_1)}{T_r * Td_{cal} * (Pd_1 - Pd_2)} \quad \text{(Equation 2)}$$

This allows a user to quickly calibrate a particular piston or dispensing chamber using factory calibration data, and temperature and pressure data available in the unit under discussion. This correction may be applied to a variety of mechanical configurations, a few of which may also be described below. In other embodiments, the temperature of the disposable $T_d$ may be estimated using the membrane temperature, $T_m$.

The corrected volume of air pumped by the disposable may then be used to pump the correct amount of dialysate. In one example, the expected value of a single stroke of a disposable chamber is 20.0 ml, and the actual volume is 20.8. A normal dialysis session, delivering 2000 ml, would require 100 pumping chamber strokes. In this instance, each stroke would deliver 0.8 ml extra, and fewer strokes may be required to deliver 2000 ml. The dialysis machine may be programmed to keep track of the volume, which for the sake of simplicity, is assumed to be constant on each stroke. As the session nears its end, say 95 strokes, a total of about 1976 ml will have been delivered. Thus, only 1 additional full stroke will bring the total to about 1997 ml. The disposable may then use mini or partial strokes to bring the total to 2000 ml or may be programmed to stop when the total volume is within, say, 0.5% or 1%. In this instance, the correction avoids 4 extra stokes, about 83 ml, a 4% error.

Temperature Control

Even with good temperature compensation, as described above, it would be desirable, and the patient may prefer, that an active form of temperature control should be exercised. For example, gentle warming of the dialysate fluid to body temperature, along with all other components of the system, would minimize the need for temperature compensation, because the fluid and all measuring and dispensing tools would be at the same (body) temperature. In another aspect, the time required for the pumping and dispensing unit to reach thermal equilibrium is reduced and the thermal mismatch between the components and body temperature is minimized. The temperature compensation discussed above may still be applied, but overall patient comfort is increased, as is the accuracy of the fluid measurement. In still another aspect, a direct reading of the dialysate fluid temperature may be taken with a thermocouple, thermistor, or other temperature sensor or temperature element placed into the dialysate fluid itself rather than into the pneumatic paths.

Figure 3:
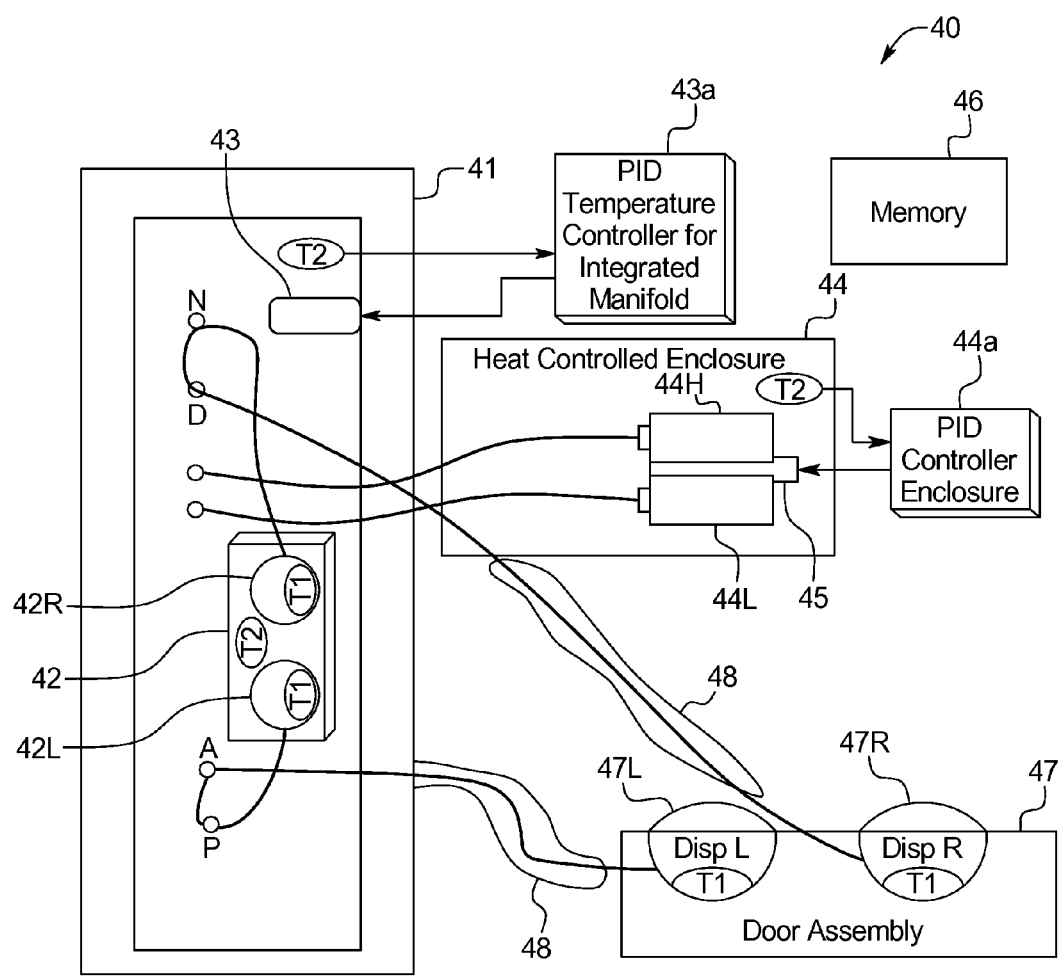
FIG. 3 depicts a system for an actively controlled pneumatic path with temperature compensation.

FIG. 3 discloses a dialysate fluid dispensing system with temperature control, with which temperature compensation may also be used. The fluid pumping system 40 includes at least on memory 46, an enclosed manifold 41 with a precision reference volume 42 and a strip heater 43 for maintaining a desired temperature. The system also includes a heat controlled enclosure 44 for the positive and negative tanks 44H, 44L, and a door assembly 47 with integral dispensing chambers or pistons 47L and 47R. A number of temperature sensors, as will be explained, are used throughout the system. In addition, insulation 48 is preferably used for the tubing that connects the various parts of the system. The insulation need not be complicated, and may be simple runs of foam between the enclosures. As will be recognized by those having ordinary skill in this art, all of these components may reside in a peritoneal dialysis system, which will include a housing for most of the above components, including a door for the disposables and a warming tray for a bag of dialysate fluid. It is preferable if the fluid pumping system components as depicted in FIG. 3 are made part of an integrated door assembly. This places many parts close together and for all practical purpose, integrates them into the door assembly. Many of these components are disclosed and explained in U.S. Pat. No. 5,474,683, which is hereby incorporated by reference, as though each page were explicitly set forth in this patent.

Enclosed manifold 41 may be enclosed within the system housing by thin layers of foam or other insulation. The manifold encloses a number of components which are not shown. These typically include a manifold assembly, a top plate, bottom plate, pressure bladder, occluder bladder, and a number of in and out pneumatic valves. While temperature compensation is important, it is recognized that the temperature differential in most instances will be limited to a difference from room temperature, 25C (77° F.), to body temperature, about 37C (98.6° F.), for a twelve-degree C. temperature gradient. From the perspective of the patient receiving cool fluid into a bloodstream, this is a significant difference. Even in an extreme situation, perhaps 20C (68° F.), the gradient would be at most 17C (about 30° F.) temperature difference. From a heat-transfer perspective, however, the temperature difference, or driving force for heat transfer, is relatively small. The manifold enclosure provides a relatively uniform temperature. The manifold enclosure includes a reference chamber 42, which includes separate left and right reference volumes, 42L, 42R, and also includes at least part of the tubing that connects the reference chamber to positive and negative tanks 44H, 44L, and to the pistons 47R, 47L. Chamber 42 may be an aluminum block, or may be made of another material. Alternately, the chambers may be separate pieces. Chamber 41 may also house valves A, P, N, D for operating the pneumatic system.

The reference chamber and the tubing (pneumatic pathways) are heated by one or more heaters, such as electric tape strip heaters 43. The heaters may be applied directly to the surfaces of the reference chamber and the tubing, or may be placed elsewhere with the manifold. The heaters are preferably controlled by at least one controller 43a using a PID control scheme. Other control schemes, such as using pulse-width-modulation may be used instead. At least one temperature sensor, T1 should be applied to each reference chamber, and preferably another, T2, at another point within the enclosure, to provide feedback to the controller. The temperature of the reference volumes, 42L, 42R, may be used as $T_r$, in the temperature compensation method described above.

As is well known, the positive and negative tanks 44H, 44L, are typically placed close to the reference chamber(s). In this embodiment, the tanks are enclosed with a heat-controlled enclosure 44, the tanks in contact with a heater 45. Heater 45 may be a heater rod, a strip heater, or other heater sufficient for mild warming of the tanks Enclosure 44 may include strips of insulating plastic or foam, and should include at least one temperature sensor T2 to provide feedback to a temperature controller 44a for controlling the temperature of enclosure 44. Enclosure 44 will also enclose some of the tubing that connects tanks 44H, 44L to the valves within enclosed manifold 41. The valves for tanks 44H, 44L may also be enclosed within enclosure 44.

The door assembly 47 housing the dispensing chambers or pistons 47L, 47R. Each piston is preferably equipped with a temperature sensor T1, the temperature sensors each sending a signal back to a controller for the pneumatic pumping system. This temperature, Td, may be used in the temperature compensation method described above, and may also be displayed, for instance on a digital readout of the controller. It has been found that some temperature sensors are preferred. In the discussions above, the preferred temperature sensor T1 may be a type K thermocouple with a very fast time constant, such as 0.005 seconds. Temperature sensor T2 may be a slower-acting type K thermocouple. Other types of thermocouples may be used, and thermistors or other temperature sensors may be used. These are merely the preferred elements.

Figure 4:
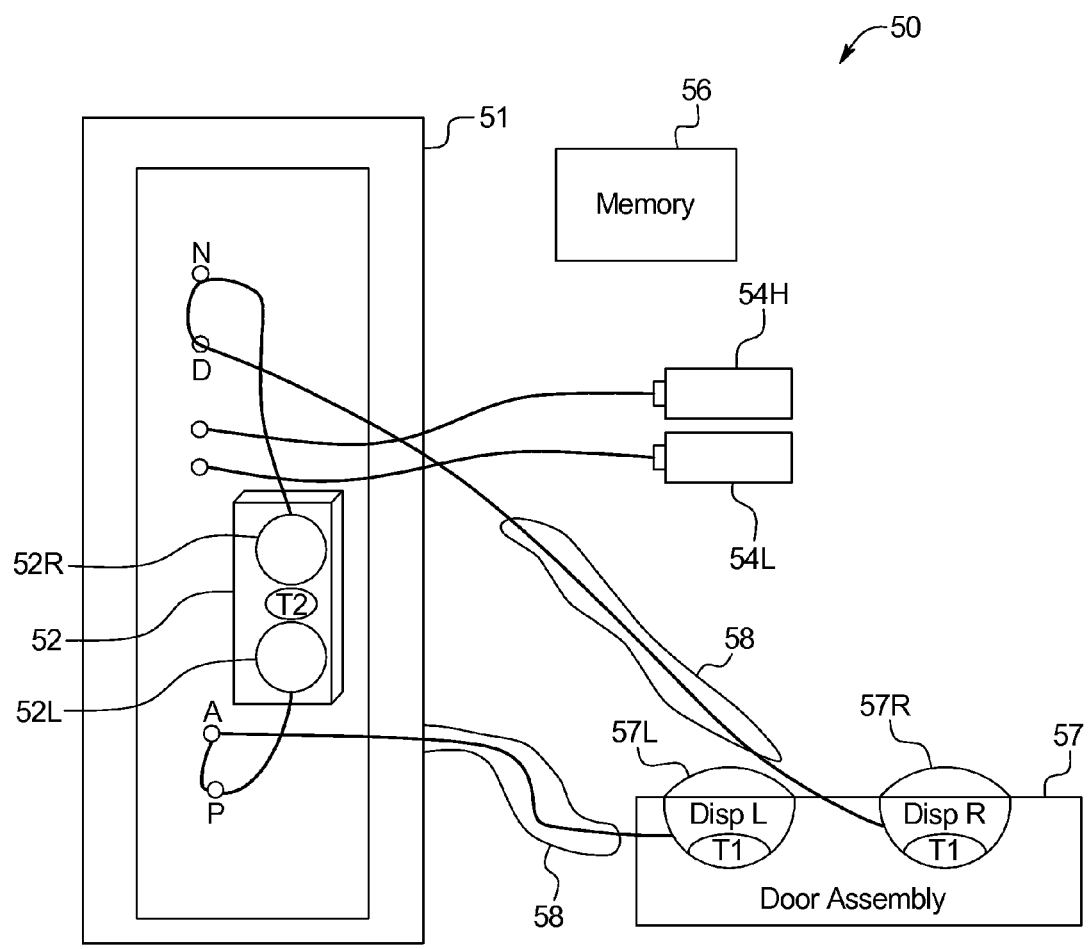
FIG. 4 depicts a system for a minimally active controlled pneumatic path.

It will be recognized that the thermal insulation and thermal control scheme of FIG. 3 is an excellent, though complicated, embodiment. It may be possible to implement a lesser degree of insulation and control, while retaining most of the advantages of the system of FIG. 3. A less-complicated embodiment is depicted in FIG. 4. In this embodiment of a temperature control system 50 for a pneumatic fluid pumping system having at least one memory 56, the reference chambers 52L, 52R are enclosed and insulated in a enclosed manifold 51, again with at least one temperature sensor T2, attached to an aluminum block 52 that may include chambers 52L, 52R. The temperature from this sensor may be used as $T_r$. Only the tubing 58 that directly connects the reference chambers to the disposables 57L, 57R is insulated. The disposables or pistons 57L, 57R, remain within the door assembly 57, each preferably equipped with a T1 sensor that may be used as $T_d$, e.g., $T_{d-l}$ or $T_{d-r}$, respectively for the left and right pistons. The positive and negative tanks 54H, 54L may not be inside a heat-controlled enclosure. It will be recognized, however, that there is little wasted space within the housing that encloses the elements of a pneumatic pumping system. The heat given off by a positive tank from warmer air when it is filled may be absorbed by the surroundings. If there is an appreciable cooling effect from the negative tank, it will likely be minimal, and will be also compensated for by its surroundings. Some of these negative effects can be overcome by enclosing the components of system 50 into an integrated door assembly.

Thermal Results

A number of experiments were conducted using the pneumatic pumping systems described above. In these experiments, an aluminum reference chamber was used, attached to a pneumatic pressure distribution manifold with thermal-conducting grease. The air tanks and tubing, including the tubing to the disposables (pistons) were insulated. Fast thermocouples were mounted to the left and right reference chambers and to the left and right pistons. The membrane between the pistons and the diaphragm of the cassette was equipped with a fast thermocouple, and the manifold itself with a slow thermocouple. The manifold, reference chamber, air tanks, and tubes were heated to abut 56C.

Figure 5:
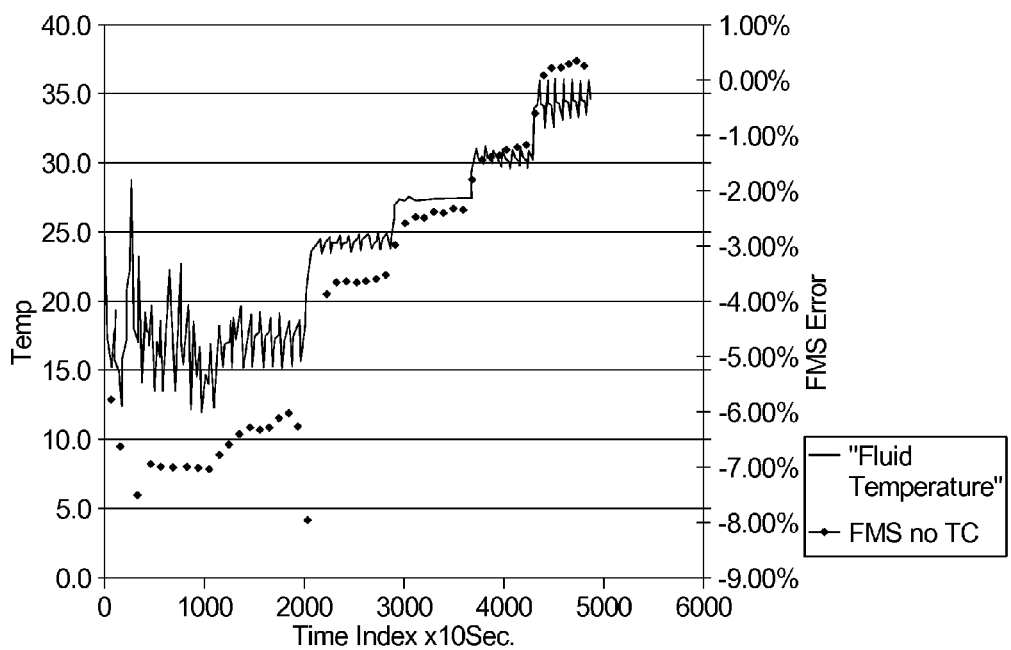
FIG. 5 depicts temperature error in prior art pneumatic systems.

In one series of experiments, as shown in FIG. 5, precision scale measurements of pumped fluid volume were compared to nominal volumes with no temperature correction applied. This series of experiments concerns dialysis fluid pumped to the patient. The left vertical axis represents the actual temperature of the dialysis fluid that was pumped, in degrees C., and the right vertical axis represents the volumetric error. The continuous line, labeled fluid temperature, is the actual temperature and the unitary dots represent the corresponding error, with no temperature correction (no TC). The horizontal axis represents the time over which the experiments took place. One conclusion is that the error is correlated to temperature, and the greater the temperature difference (from body temperature, 37C), the greater the volumetric error. Both the volumetric and temperature data have been averaged for the left and right sides of the disposable or pistons. Each dot represents about 1000 ml of transferred fluid.

Figure 6:
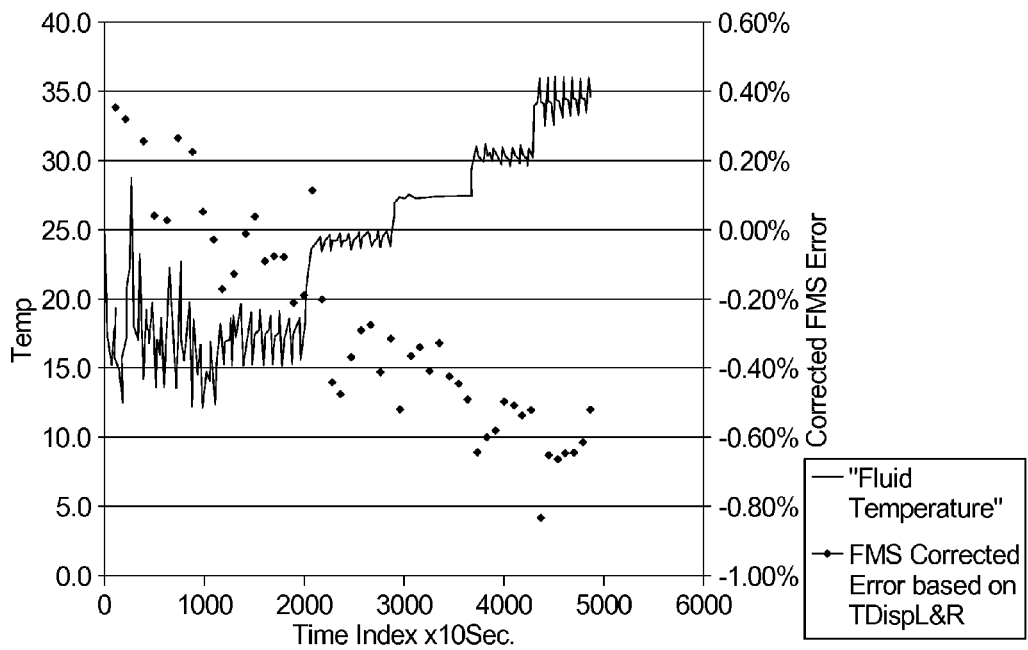
FIG. 6 depicts temperature error in fluid pumped to a patient.

Another series of experiments was conducted, using the temperature correction discussed above and incorporated as Equation 2 above. These experiments are depicted in FIG. 6, using the experimental setup and the same framework as that of FIG. 5. The continuous line represents the actual fluid temperature, while the unitary dots represent error, based on the fluid management system (FMS) corrected error, based on the temperature of the right and left disposables (TDispL& R). In this set of experiments, the error is greatly reduced, with extremes of about positive 0.30% when the dialysate temperature is cool (15 C) and about negative 0.60% when the dialysate is at 35 C. This contrasts with an error of about 7% with no temperature compensation, as shown in FIG. 5. Accordingly, the temperature compensation of Equation 2 significantly reduces volumetric error in dispensing dialysis fluid to a patient.

Figure 7:
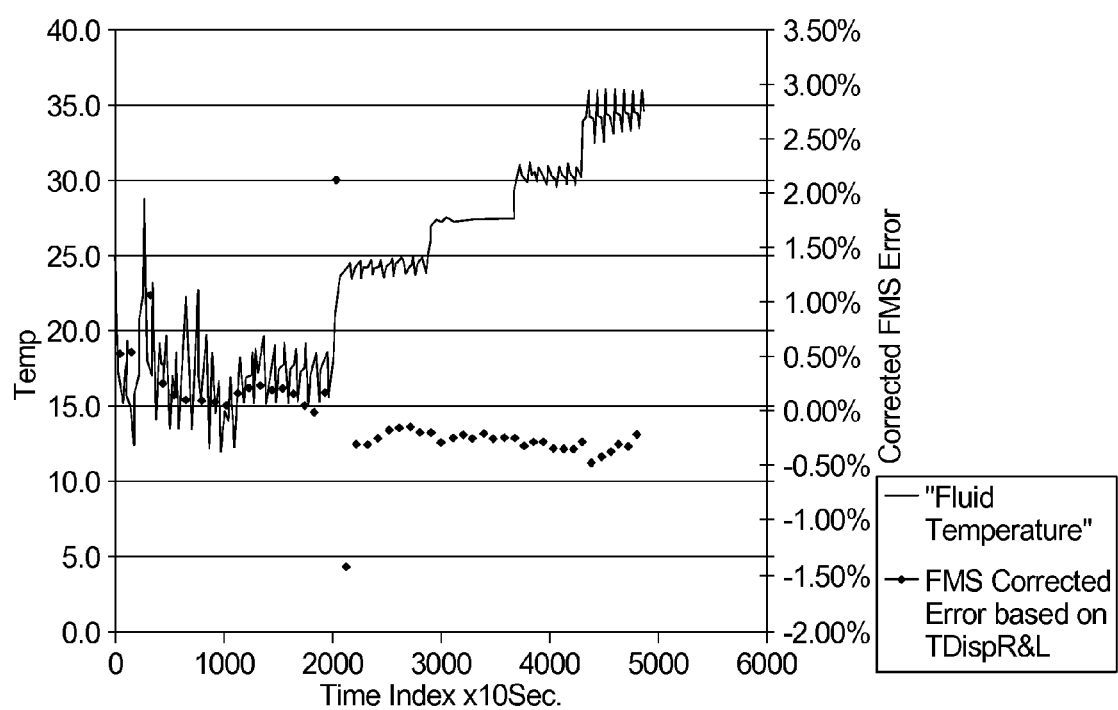
FIG. 7 depicts temperature error in fluid pumped from a patient.

Even greater error correction was achieved in measuring the volumes of dialysate pumped from the patient, as shown in FIG. 7. These experiments were conducted in the same manner as the above, with the continuous line representing actual fluid temperature, and the volumetric error represented by unitary dots. Errors in fluid volume pumped are again very low, now from about positive 0.50% to about negative 0.50%, with fluid temperatures ranging from 15C to about 35C. Again, both the volumetric and temperature data have been averaged for the left and right sides of the disposable or pistons. Each dot represents about 1000 ml of transferred fluid.

Direct Fluid Measurement

Another improvement is the elimination of one or more temperature sensors within the dispensing chambers or pistons. Instead of using sensors in these chambers, it is possible to mount a temperature sensor, such as a thermocouple, directly in the dialysate outlet line, such as the outlet of the left or right dispensing chamber, or both. Using these temperatures, an estimate of $T_d$, for either the right or left piston, or both, may then be made. Once the pneumatic pumping system is in a steady-state operating condition, temperature correction is fairly straight-forward, as noted above. However, until that state is reached, relatively cooler fluid being pumped cools the membrane and the areas in contact with the membrane. The temperature of the pumped dialysate fluid will therefore lag the temperature of the air used to pump the fluid. A time constant, or temperature lag, can be established empirically and used to apply measured fluid temperature correction to the piston or dispensing chamber temperature. The pneumatic pumping system can then be programmed to apply this correction or lag to correct the predicted piston temperatures of each chamber in order to compensate for pneumatic volume, as discussed above in the section on thermal compensation.

Figure 8:
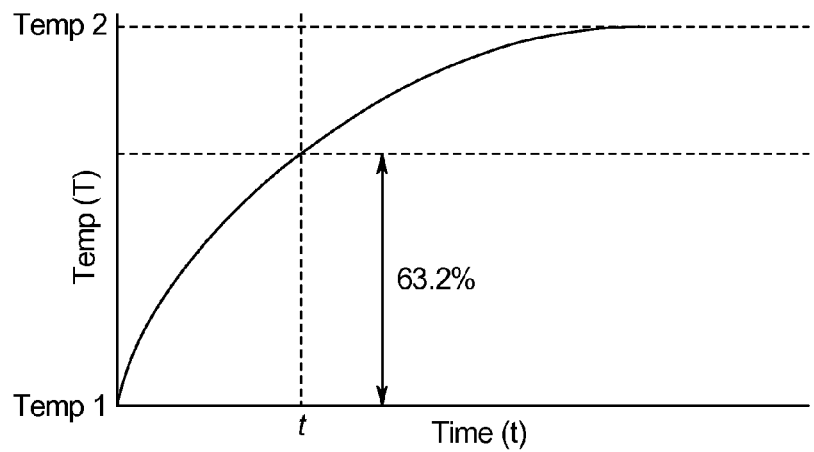
FIG. 8 depicts time lag between start-up and the time the piston achieves thermal steady-state or equilibrium temperature.
Figure 9:
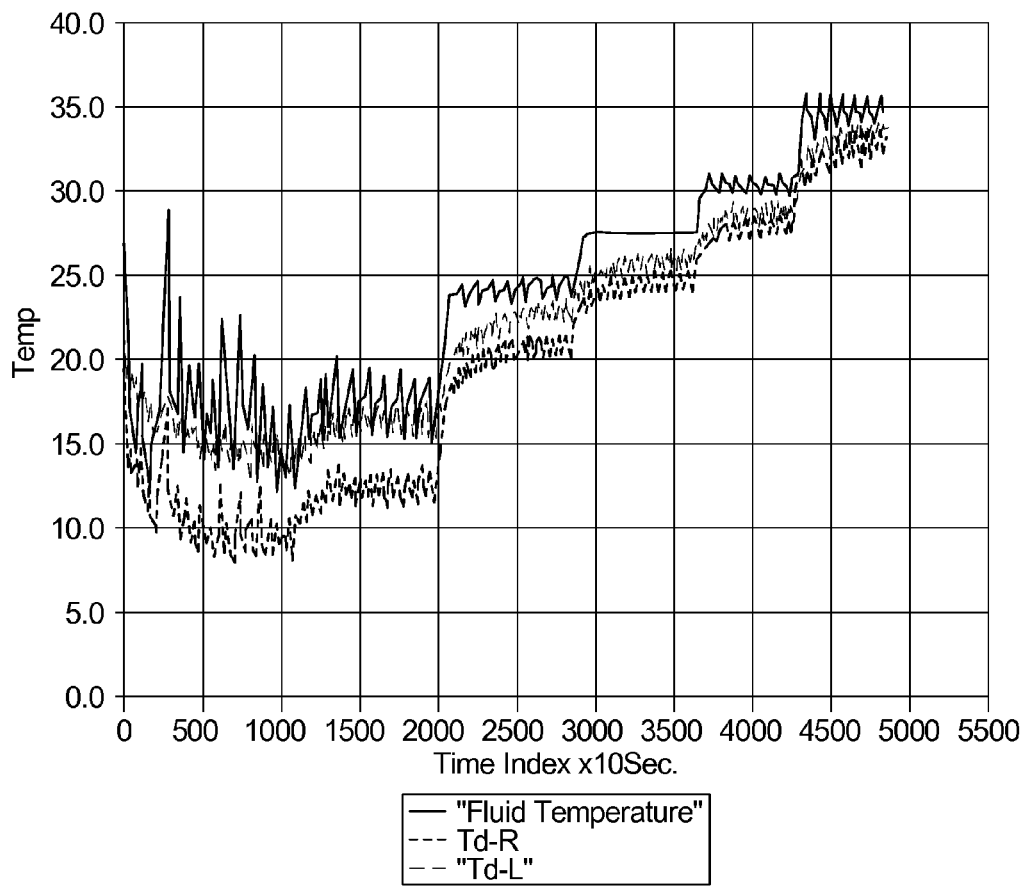
FIG. 9 depicts the time lag and temperature differences between the dialysate fluid and the pistons.

An illustration of the thermal lag problem is depicted in FIG. 8. The temperature of the piston or dispensing chamber at start-up is Temp1, while the temperature which it will eventually reach is Temp2. In most instances, Temp1 will be at a lower temperature, while Temp2 will be higher, but the principle applies to corrections in either direction. It will take a finite period of time until the system comes to a steady state and the two temperatures are equal, and the error in the interim is the difference between the two temperatures. FIGS. 9 and 10 depict the result of tests to determine thermal lag and the differences in actual operating systems. FIG. 9 depicts the temperature in the left and right dispensing chambers or pistons, $T_{d-l}$ and $T_{d-r}$, as compared with the actual temperature of dialysate fluid, fluid temperature. As the graph shows, the dialysate temperature, fluid temperature, change leads the piston temperature change by as much as 7 or 8 degrees C. for many minutes, even hours. Each horizontal marker is 5000 seconds, the 500 units indicated, multiplied by 10 sec. As can also be seen in FIG. 9, there is an offset between the fluid temperature, the solid line, and the temperature of the pistons does not reach the fluid temperature.

In FIG. 10, an estimate is made of the temperature of the combined left and right chambers, and is displayed on the graph as the dashed line. This estimate may then be applied as a correction factor, or offset, to the measured temperature of dialysate fluid, and used in an estimate of the piston temperatures. The estimate may be made by calculating an ultimate temperature difference, taking the 63.2% value of the difference, and then adding that value to the detected temperature. For instance, in FIG. 10, $T_1$ for $T_{d-l}$ is taken early in the process, as 12.5, while $T_2$ for $T_{d-r}$ is 16.3. In both cases, an estimate for the next temperature, $T_2$, is taken by letting $T_2$ equal the actual measured temperature of the dialysate less an offset temperature. The offset temperature is taken as $(1-e^{t/\tau})$ multiplied by the difference between the first temperature and the dialysate temperature, where t is the estimated time lag in seconds and $\tau$ is a time constant that is derived from the calibration value when the chambers are calibrated. In testing, the value of $\tau$ was determined to be 67 seconds and 197 seconds in different experiments for different disposable configurations. Table 1 with the results is shown below. The temperature was measured precisely, to a tenth of a degree, and the correlation for accuracy is within about 1 degree. Thus, even though temperature $T_2$ and $T_{offset}$ should add up to the long-term equilibrium value, 24C, there is a discrepancy of +0.2° C. for $T_{d-r}$ and +0.8° C. for $T_{d-l}$.

TABLE 1

Estimating Piston Temperature using Disposable/Membrane/Foam and Thermal Time Constant

| | Column | | | | | | |
|---|---|---|---|---|---|---|---|
| Chamber | 1<br>$T_1$ | 2<br>$T_2$ | 3<br>Delta T,<br>° C. | 4<br>Delta C *<br>0.632 | 5<br>$T_1$ +<br>col. 4 | 6<br>Tau<br>(63.2%) | 7<br>$T_{offset}$<br>° C.<br>(@24 C.) |
| $T_{d-r}$ | 12.5 | 20.9 | 8.4 | 5.3 | 17.8 | 67 | −3.3 |
| $T_{d-l}$ | 16.3 | 22.9 | 6.6 | 4.2 | 20.5 | 197 | −1.9 |

The value of $\tau$ will depend on the particular design of the pumping chamber, and may also vary with the particular ambient temperature of the apparatus. Thus, the particular offset temperature used in the calculation will also vary depending on the pumping chamber itself, or at least its design, and the temperature of the pumping chamber. As also noted above, there can be significant differences between left and right chambers in the same machine. This may be due to the environment within the disposable or the dialysis machine, such as the precise location of sources of heat and cold with respect to the left and right pumping chambers. The difference may also be due to minute differences in the room in which dialysis takes place, such as one side of the room being a few degrees warmer or cooler. There may be a source of cooled or heated air that impacts the dialysis machine, and the left and right chambers, in different ways, if the left or right chamber is closer to the source or heating or cooling, and thus one side is more affected than the other.

Thus, the offset temperatures are calculated and applied to the fluid temperatures as the best estimate of $T_{d-l}$ or $T_{d-r}$. This estimated internal temperature of the piston or dispensing chamber is then applied to Equation 2 above. In a preferred embodiment, a look-up table of offsets may be constructed and held in the memory of the system controller (e.g, memory 46 or 56 shown in FIGS. 3 and 4). As an alternative, an estimate may be made for the particular dialysate system, or type of system, as a generalized indicator of thermal performance. An example is shown in FIG. 11. A temperature error is graphed on the vertical axis and is well correlated with the average dialysate fluid temperature (both in degrees C.) on the horizontal axis. In one embodiment, the estimates of $T_{d-l}$ and $T_{d-r}$ are averaged and are correlated as shown in FIG. 11. The correlation is stored in a look-up table in the memory of the system controller (e.g, memory 46 or 56 shown in FIGS. 3 and 4). The temperature of the air was determined by a thermocouple placed in the reference chamber. The error was determined by thermocouples placed in the dialysate fluid itself to check the temperature difference. In this series of experiments, the system included a heated manifold and heated air tanks, as shown in FIG. 3, all at 57C. The correlation was very high, $R^2$ about 0.96.

Figure 12:
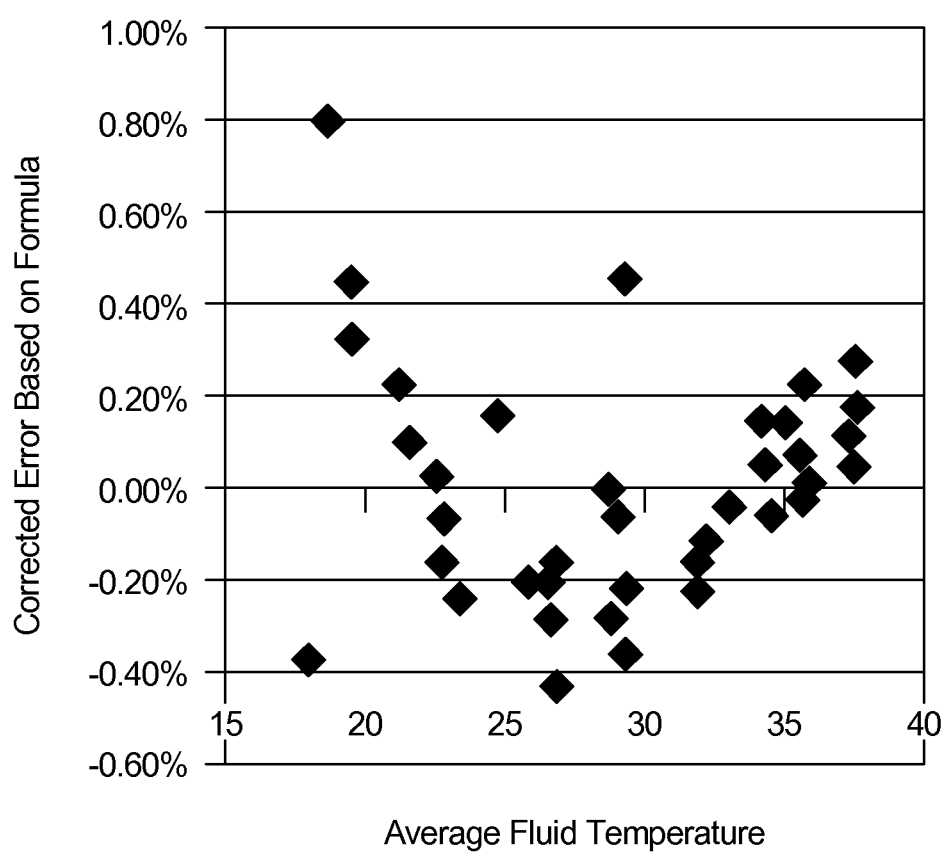
FIG. 12 depicts the volumetric error based on a second method of applying a steady-state temperature offset for a pneumatic pumping system.

As noted above, the temperature of the dialysate fluid itself may be used, rather than relying on estimates from the pneumatic system. One additional correction has also been discovered that is based on the fluid temperature alone. In calculating the volume of dialysate fluid, we have found that the temperature of the fluid itself may cause an additional error. Our results are shown in FIG. 12, which charts an error in fluid volume against the temperature of the fluid itself. Our results show that the error correlates with a particular correction, i.e., the true volume delivered equals the indicated volume multiplied by a correction factor. The correction factor is (−0.0014*fluid temp in degrees C.)+1.0539. As an example, if the fluid temperature is 25 C, the correction factor is −0.0035+1.0539, for a total of 1.0504. If the indicated volume is 1000 ml, the actual delivered volume was 1050 ml. Thus, if 1000 ml is meant for delivery, only 952 ml should be delivered. This result was confirmed by experimenting with water and measuring the mass of the volume.

Figure 13:
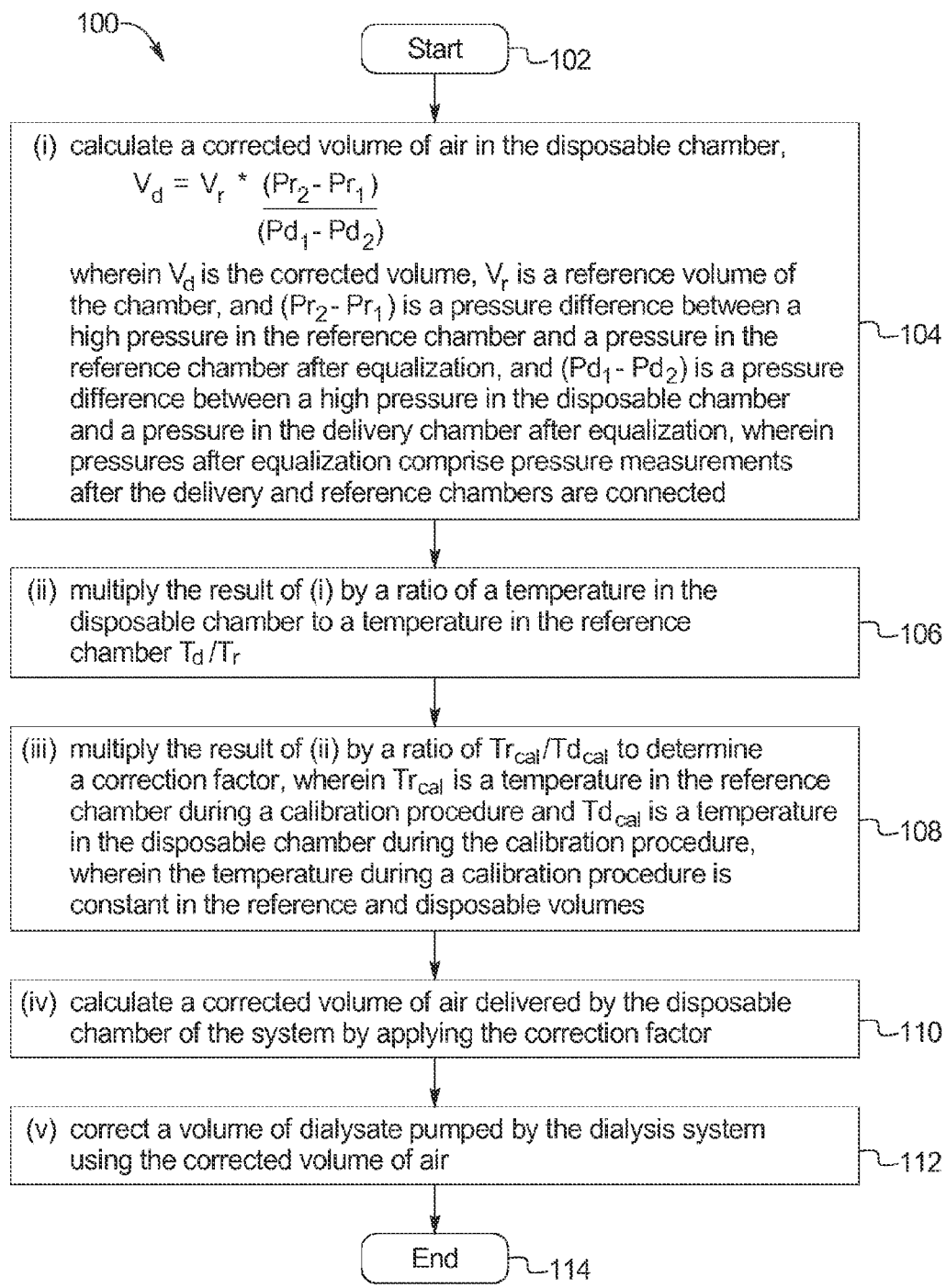
FIG. 13 is a flow diagram illustrating one embodiment of a method of the present disclosure of compentsating for temperature error in a pnematic pumping system.

Referring now to FIG. 13, method 100 illustrates one embodiment for compensating for temperatures error in a system of the present disclosure. Upon starting method 100 as illustrated at oval 102, method 100 (i) calculates a corrected volume of air in a disposable chamber via the following algorithm, $$V_d = V_r * (Pr_2 - Pr_1)/(Pd_1 - Pd_2)$$

wherein $V_d$ is the corrected volume, $V_r$ is a reference volume of the chamber, and (Pr2−Pr1) is a pressure difference between a high pressure in the reference chamber and a pressure in the reference chamber after equalization, and (Pd1−Pd2) is a pressure difference between a high pressure in the disposable chamber and a pressure in the delivery chamber after equalization, wherein pressures after equalization comprise pressure measurements after the delivery and reference chambers are connected, as illustrated by block 104. At block 106, method 100 (ii) multiplies the result of (i) by a ratio of a temperature in the disposable chamber to a temperature in the reference chamber $T_d/T_r$. At block 108, method 100 (iii) multiplies the result of (ii) by a ratio of $Tr_{cal}/Td_{cal}$ to determine a correction factor, wherein $Tr_{cal}$ is a temperature in the reference chamber during a calibration procedure and $Td_{cal}$ is a temperature in the disposable chamber during the calibration procedure, wherein the temperature during a calibration procedure is constant in the reference and disposable volumes, as illustrated by block 108. At block 110, method 100 (iv) calculates a corrected volume of air delivered by the disposable chamber of the system by applying the correction factor. At block 112, method 100 (v) corrects a volume of dialysate pumped by the dialysis system using the corrected volume of air, as illustrated by block 112. At oval 114, method 100 ends.

Figure 14:
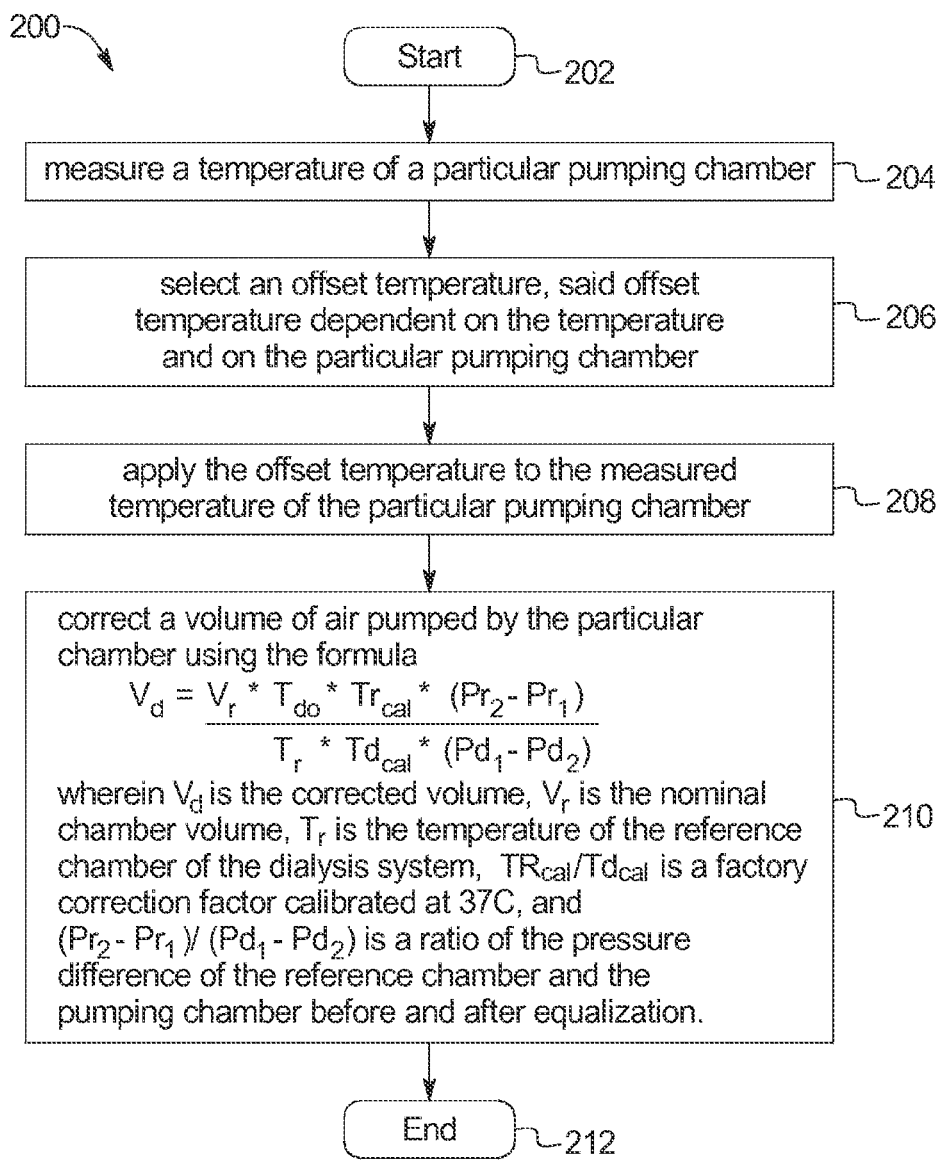
FIG. 14 is a flow diagram illustrating one embodiment of a method of the present disclosure of compentsating for temperature error in a dialysis system.

Referring now to FIG. 14, method 200 illustrates another embodiment for compensating for temperature errors in a system of the present disclosure. Upon starting method 200 as illustrated at oval 202, method 200 measures a temperature of a particular pumping chamber as illustrated by block 204. At block 206, method 200 selects an offset temperature, which is dependent on the temperature and on a particular pumping chamber. At block 208, method 200 applies the offset temperature to the measured temperature of the particular pumping chamber. At block 210, method 200 corrects a volume of air pumped by the particular pumping chamber using the formula, $$V_d = (V_r * T_{do} * Tr_{cal} * (Pr_2 - Pr_1))/(T_r * Td_{cal} * (Pd_1 - Pd_2))$$

wherein Vd is the corrected volume, Vr is the nominal chamber volume, Tdo is the temperature of the chamber with the offset applied, Tr is the temperature of the reference chamber of the dialysis system, Trcal/Tdcal is a factory correction factor calibrated at 37C, and (Pr2−Pr1)/(Pd1−Pd2) is a ratio of the pressure differences of the reference chamber and the pumping chamber before and after equalization, as illustrated by block 210. At oval 212, method 200 ends.

Figure 15:
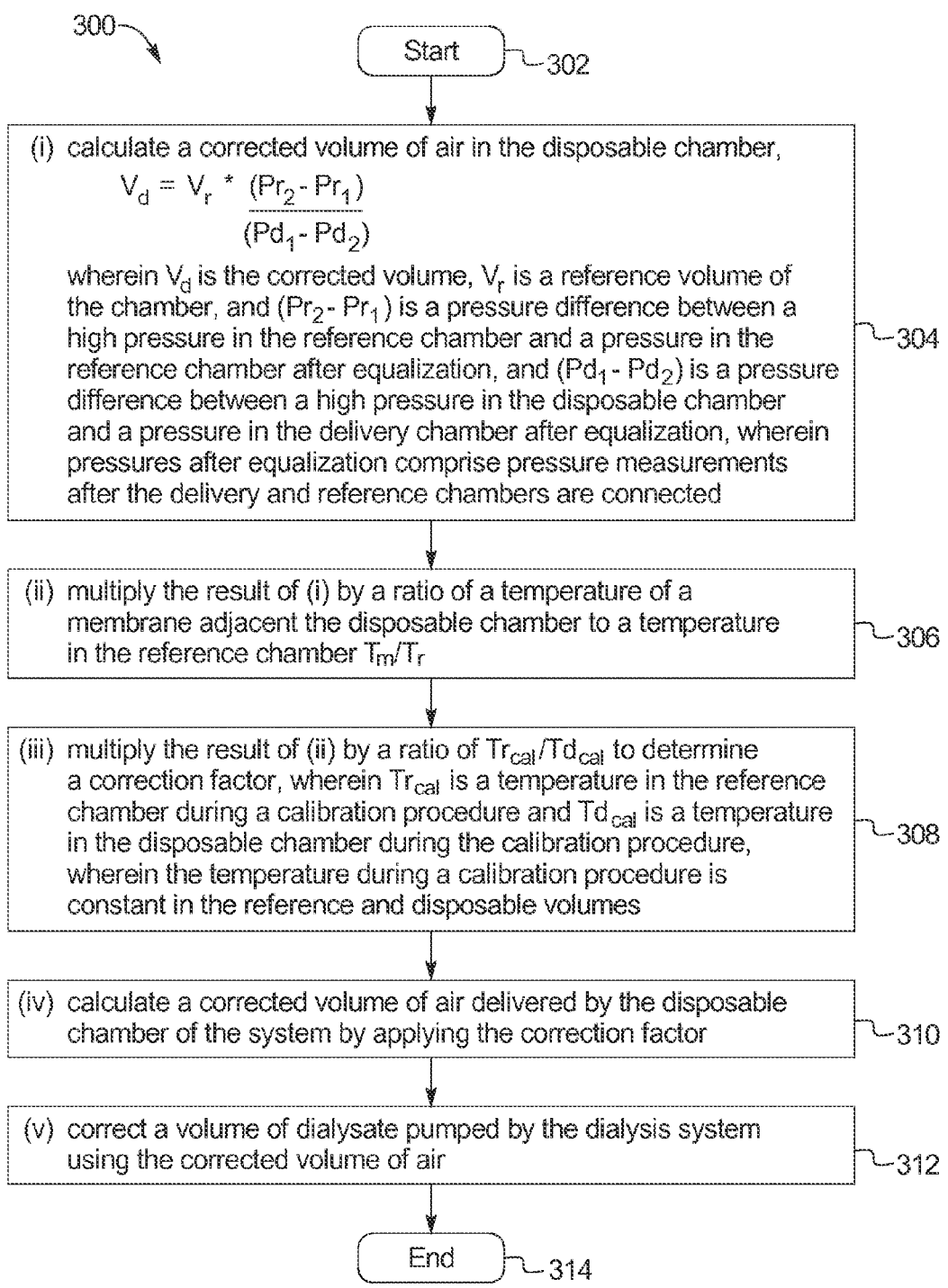
FIG. 15 is a flow diagram illustrating one embodiment of a method of the present disclosure of compentsating for temperature error in a pnematic pumping system.

Referring now to FIG. 15, method 300 illustrates a further embodiment for compensating for temperature error in a system of the present disclosure. Upon starting method 300 as illustrated at oval 302, method 300 (i) calculates a corrected volume of air in a disposable chamber, $$V_d = V_r * (Pr_2 - Pr_1)/(Pd_1 - Pd_2)$$

wherein Vd is the corrected volume, Vr is a reference volume of the chamber, and (Pr2−Pr1) is a pressure difference between a high pressure in the reference chamber and a pressure in the reference chamber after equalization, and (Pd1−Pd2) is a pressure difference between a high pressure in the disposable chamber and a pressure in the delivery chamber after equalization, wherein pressures after equalization comprise pressure measurements after the delivery and reference chambers are connected, as illustrated by block 304. At block 306, method 300 (ii) multiplies the result of (i) by a ratio of a temperature of a membrane adjacent the disposable chamber to a temperature in the reference chamber, Tm/Tr. At block 308, method 300 (iii) multiplies the result of (ii) by a ratio of Trcal/Tdcal to determine a correction factor, wherein Trcal is a temperature in the reference chamber during a calibration procedure and Tdcal is a temperature in the disposable chamber during the calibration procedure, wherein the temperature during a calibration procedure is constant in the reference and disposable volumes. At block 310, method 300 (iv) calculates a corrected volume of air delivered by the disposable chamber of the system by applying the correction factor. At block 312, method 300 (v) corrects a volume of dialysate pumped by the dialysis system using the corrected volume of air. At oval 314, method 300 ends.

Figure 16:
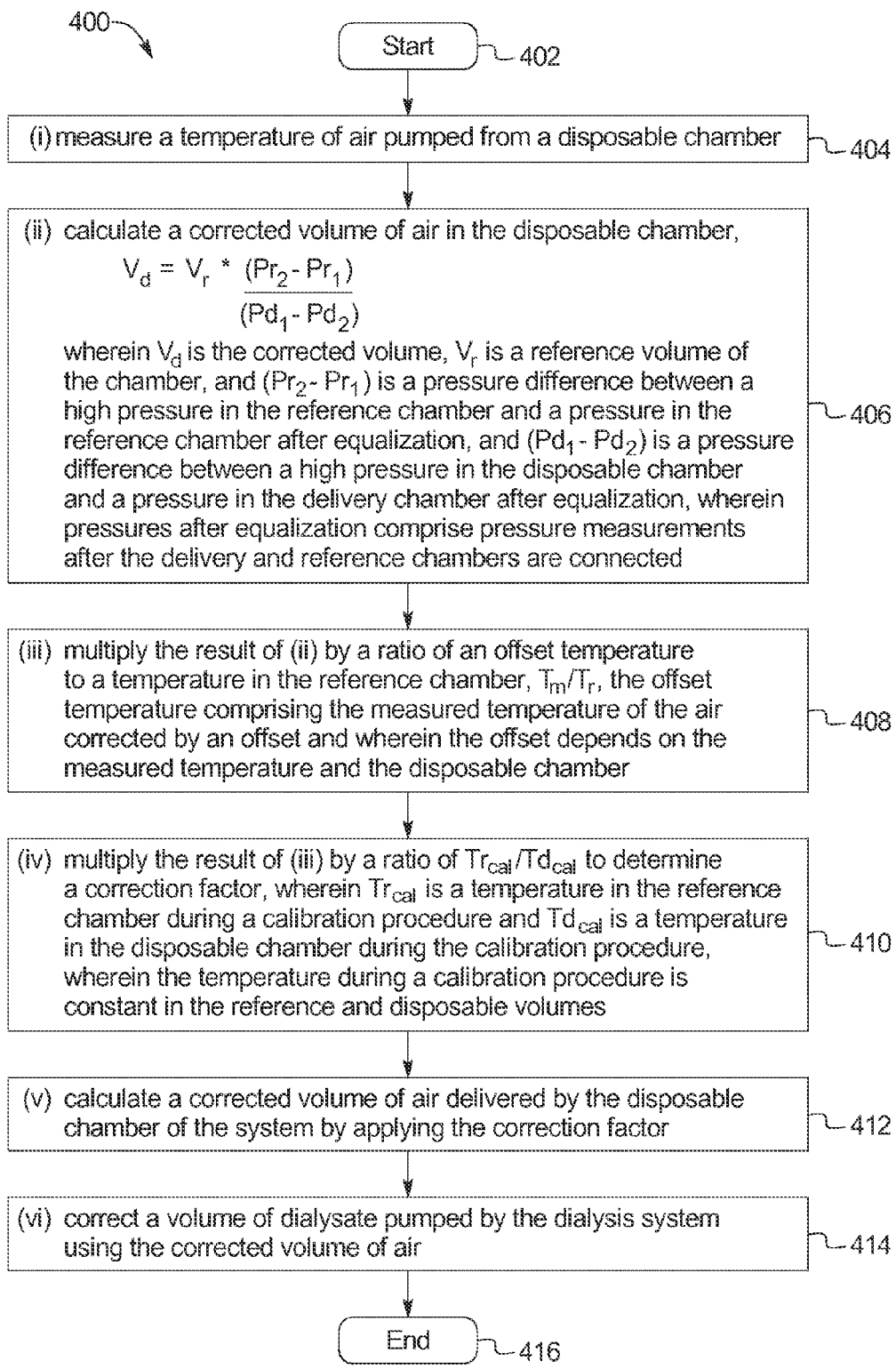
FIG. 16 is a flow diagram illustrating one embodiment of a method of the present disclosure of compentsating for temperature error in a pnematic pumping system.

Referring now to FIG. 16, method 400 illustrates yet another embodiment for compensating for temperature error in a system of the present invention. Upon starting method 400 as illustrated at oval 402, method 400 (i) measures a temperature of air pumped from a disposable chamber, as illustrated by block 404. At block 406, method 400 (ii) calculates a corrected volume of air in the disposable chamber, $$V_d = V_r * (Pr_2 - Pr_1)/(Pd_1 - Pd_2)$$

wherein Vd is the corrected volume, Vr is a reference volume of the chamber, and (Pr2−Pr1) is a pressure difference between a high pressure in the reference chamber and a pressure in the reference chamber after equalization, and (Pd1−Pd2) is a pressure difference between a high pressure in the disposable chamber and a pressure in the delivery chamber after equalization, wherein pressures after equalization comprise pressure measurements after the delivery and reference chambers are connected. At block 408, method 400 (iii) multiplies the result of (ii) by a ratio of an offset temperature to a temperature in the reference chamber, $T_m/T_r$, the offset temperature comprising the measured temperature of the air corrected by an offset and wherein the offset depends on the measured temperature and the disposable chamber. At block 410, method 400 (iv) multiplies the result of (iii) by a ratio of $Tr_{cal}/Td_{cal}$ to determine a correction factor, wherein $Tr_{cal}$ is a temperature in the reference chamber during a calibration procedure and $Td_{cal}$ is a temperature in the disposable chamber during the calibration procedure, wherein the temperature during a calibration procedure is constant in the reference and disposable volumes. At block 412, method 400 (v) calculates a corrected volume of air delivered by the disposable chamber of the system by applying the correction factor. At block 414, method 400 (vi) corrects a volume of dialysate pumped by the dialysis system using the corrected volume of air. At oval 416, method 400 ends.

Figure 17:
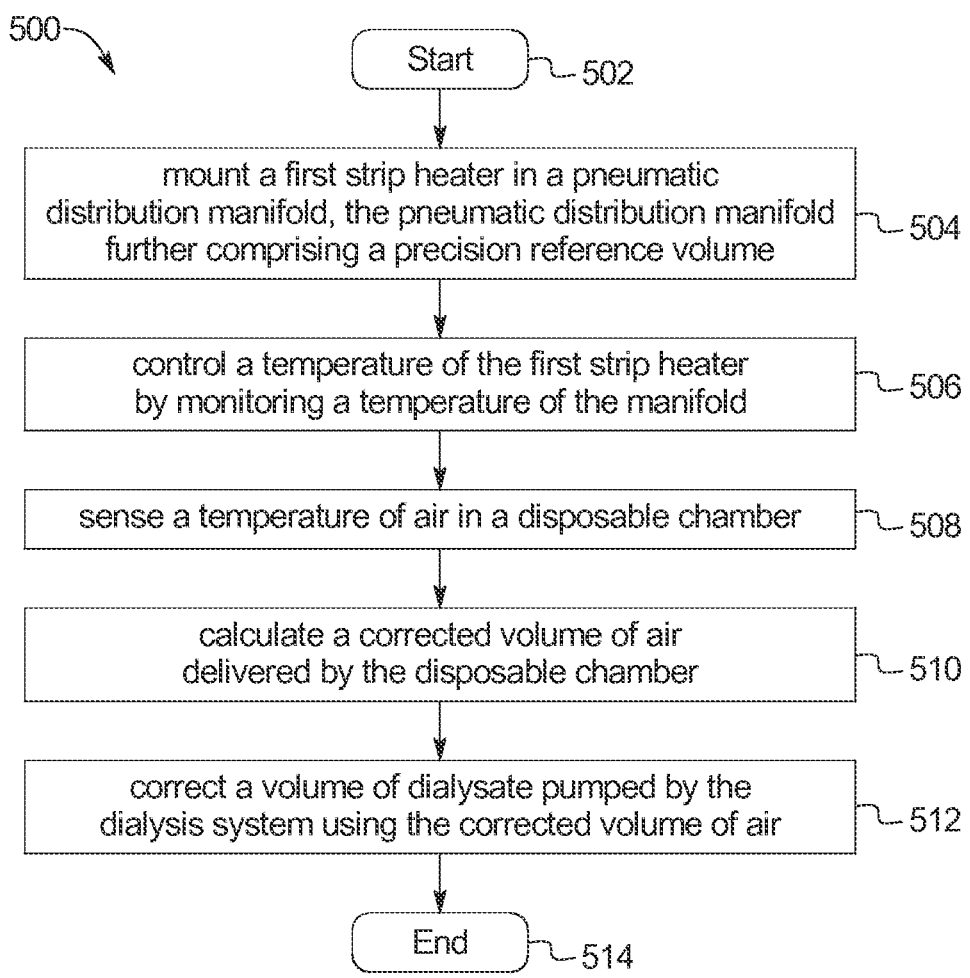
FIG. 17 is a flow diagram illustrating one embodiment of a method of the present disclosure of controlling pneumatic air temperature in a dialysis system.

Referring now to FIG. 17, method 500 illustrates an embodiment for controlling pneumatic air temperature in a system of the present invention. Upon starting method 500 as illustrated at oval 502, method 500 mounts a first strip heater in a pneumatic distribution manifold, the pneumatic distribution manifold further comprising a precision reference volume, as illustrated by block 504. Method 500 controls a temperature of the first strip heater by monitoring a temperature of the manifold, as illustrated by block 506. Method 500 further senses a temperature of air in a disposable chamber, as illustrated by block 508. Method 500 calculates a corrected volume of air delivered by the disposable chamber, as illustrated by block 510. Method 500 corrects a volume of dialysate pumped by the dialysis system using the corrected volume of air, as illustrated by block 512. At oval 514, method 500 ends.

The above disclosures are not meant to limit embodiments discussed herein. For instance, referring to the temperature control portion, it is clear that the manifold enclosure may be integrated with the door assembly to achieve even greater thermal stability and thus temperature control. This integration eliminates error due to exposed tubing and could also lead to fewer heat losses simply by increased proximity of the components. The above discussions on thermal results and direct fluid measurement may then be applied to the integrated fluid management system, with the manifold enclosure with an integral door assembly experiencing smaller thermal losses and error than at present. Look up tables as discussed, for thermal lag, offsets, and so forth, may also be constructed for the integrated assembly.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A dialysis system comprising:
   a disposable cassette including a disposable chamber;
   a reference chamber; and
   a controller configured to
   (i) calculate a volume of air delivered to the disposable chamber using the formula $$V_d = V_r * \frac{(Pr_2 - Pr_1)}{(Pd_1 - Pd_2)},$$

wherein $V_d$ is the volume, $V_r$ is a reference volume of the disposable chamber, and $(Pr_2-Pr_1)$ is a difference between a pressure in the reference chamber before and after equalization, and $(Pd_1-Pd_2)$ is a difference between a pressure in the disposable chamber before and after equalization,
   (ii) calculate a corrected volume of air delivered to the disposable chamber by multiplying $V_d$ by a ratio of a temperature in the disposable chamber to a temperature in the reference chamber $T_d/T_r$, and by a ratio of $Tr_{cal}/Td_{cal}$, wherein $Tr_{cal}$ is a previously measured temperature in the reference chamber and $Td_{cal}$ is a previously measured temperature in the disposable chamber, and
   (iii) calculate a corrected volume of dialysate pumped by the dialysis system using the corrected volume of air delivered to the disposable chamber.

2. The dialysis system of claim 1, which includes an expected volume of air in the disposable chamber, and wherein the controller is configured to calculate the corrected volume of dialysate pumped by the dialysis system by adding or subtracting the corrected volume of air in the disposable chamber to or from, respectively, the corrected volume of air delivered to the disposable chamber.

3. The dialysis system of claim 1, wherein the pressures after equalization include pressure measurements after the disposable and reference chambers are pneumatically connected.

4. The dialysis system of claim 1, which includes a sensor for sensing the temperature in the disposable chamber, the sensor located (i) within the disposable chamber, or (ii) on a wall of the disposable chamber.

5. The dialysis system of claim 1, which includes two sensors, wherein the temperature of the disposable chamber is sensed by (i) one of the sensors, or (ii) each of the sensors.

6. The dialysis system of claim 1, which includes two sensors, and the temperature of the reference chamber is sensed by (i) one of the sensors, or (ii) each of sensors.

7. A dialysis system having temperature compensation comprising:
   a pumping mechanism including
   a disposable cassette including at least two pumping chambers, and
   a reference chamber; and
   a controller configured to (i) input a temperature measurement of one of the pumping chambers, (ii) select an offset temperature that is dependent on the measured temperature, (iii) apply the offset temperature to the measured temperature, and (iv) correct a volume of air pumped by the particular pumping chamber using the formula $$V_d = \frac{V_r * T_{do} * Tr_{cal} * (Pr_2 - Pr_1)}{T_r * Td_{cal} * (Pd_1 - Pd_2)},$$

wherein $V_d$ is the corrected volume, $V_r$ is a nominal chamber volume, $T_{do}$ is the temperature of the chamber with the offset applied, $T_r$ is the temperature of the reference chamber, $Tr_{cal}/Td_{cal}$ is a correction factor calibrated at 37° C., and $(Pr_2-Pr_1)/(Pd_1-Pd_2)$ is a ratio of the pressure differences of the reference chamber and the particular pumping chamber before and after equalization.

8. The dialysis system of claim 7, which includes a temperature sensor for measuring the temperature of the particular pumping chamber, the sensor located in an air path in fluid communication with the particular pumping chamber or attached to a wall inside the particular pumping chamber.

9. The method of claim 7, wherein the controller is further configured to select the offset temperature by (a) inputting a thermal time constant for the particular pump chamber, and (b) applying the thermal time constant to compensate for at least one of the temperature of the particular pump chamber and a temperature of the air pumped.

10. A peritoneal dialysis system including temperature compensation, the system comprising:
    a pumping system including
    a disposable chamber, and
    a reference chamber; and
    a controller configured to
    (i) calculate a volume of air delivered to the disposable chamber using the formula $$V_d = V_r * \frac{(Pr_2 - Pr_1)}{(Pd_1 - Pd_2)},$$

wherein $V_d$ is the volume, $V_r$ is a reference volume of the reference chamber, and $(Pr_2-Pr_1)$ is a difference between a pressure in the reference chamber before and after equalization, and $(Pd_1-Pd_2)$ is a difference between a pressure in the disposable chamber before and after equalization,
(ii) calculate a corrected volume of air delivered to the disposable chamber by multiplying $V_d$ by a ratio of a temperature of a membrane adjacent the disposable chamber to a temperature in the reference chamber, $T_m/T_r$, and by a ratio of $Tr_{cal}/Td_{cal}$, wherein $Tr_{cal}$ is a previously measured temperature in the reference chamber, and $Td_{cal}$ is a previously measured temperature in the disposable chamber, and
(iii) calculate a corrected volume of dialysate pumped by the dialysis system using the corrected volume of air delivered to the disposable chamber.

11. The peritoneal dialysis system of claim 10, which includes an expected volume of air in the disposable chamber, and wherein the controller is configured to calculate the corrected volume of dialysate pumped by the dialysis system by adding or subtracting the corrected volume of air in the disposable chamber to or from, respectively, the corrected volume of air delivered to the disposable chamber.

12. The peritoneal dialysis system of claim 10, wherein the pressures after equalization include pressure measurements after the disposable and reference chambers are pneumatically connected.

13. The peritoneal dialysis system of claim 10, wherein the controller is further configured to estimate a temperature of air of the disposable chamber and use the estimated temperature to calculate the corrected volume of air delivered to the disposable chamber.

14. The peritoneal dialysis system of claim 10, including a sensor configured to sense a temperature of air delivered to the disposable chamber, and wherein the controller is further configured to sense a temperature of air delivered to the disposable chamber via the sensor and correct the volume of air delivered to the disposable chamber using the sensed temperature.

15. A peritoneal dialysis system comprising:
a pumping system including
a pumping mechanism,
a disposable chamber, and
a reference chamber; and
a controller configured to:
(i) measure a temperature of air pumped from the disposable chamber,
(ii) calculate a volume of air delivered to the disposable chamber using the formula $$V_d = V_r * \frac{(Pr_2 - Pr_1)}{(Pd_1 - Pd_2)},$$

wherein $V_d$ is the volume, $V_r$ is a reference volume of the reference chamber, and $(Pr_2-Pr_1)$ is a difference between a pressure in the reference chamber before and after equalization, and $(Pd_1-Pd_2)$ is a difference between a pressure in the disposable chamber before after equalization,
(iii) calculate a corrected volume of air delivered to the disposable chamber by multiplying $V_d$ by:
(a) a ratio of an offset temperature to a temperature in the reference chamber, $T_m/T_r$, the offset temperature including the measured temperature of the air corrected by an offset, wherein the offset depends on the measured temperature and the disposable chamber, and
(b) a ratio of $Tr_{cal}/Td_{cal}$, wherein $Tr_{cal}$ is a previously measured temperature in the reference chamber, and $Td_{cal}$ is a previously measured temperature in the disposable chamber, and
(iii) calculate a corrected volume of dialysate pumped by the dialysis system using the corrected volume of air delivered to the disposable chamber.

16. The peritoneal dialysis system of claim 15, which includes a memory operably connected to the controller, wherein a table of offset temperatures is stored in the memory.

17. The peritoneal dialysis system of claim 15, wherein the controller is further configured to calculate the offset temperature by (a) inputting a thermal time constant for the disposable chamber, and (b) applying the thermal time constant in a correction factor to compensate for at least one of the temperature in the disposable chamber and a temperature of the air delivered.

18. A dialysis system comprising:
a pneumatic distribution manifold including
a heater, and
a reference volume chamber;
a disposable chamber; and
a controller configured to (i) control a temperature of the heater by monitoring a temperature of the manifold, (ii) monitor a temperature of air in the disposable chamber, (iii) calculate a corrected volume of air delivered to the disposable chamber using a temperature of air in the reference volume chamber, and (iv) correct a volume of dialysate pumped by the dialysis system using the calculated corrected volume of air delivered to the disposable chamber.

19. The dialysis system of claim 18, wherein the heater is a first heater, and which includes a second heater, wherein at least one of the first and second heaters is configured to include a set point that is above a desired temperature of dialysate fluid to be delivered by the dialysis system.

20. The dialysis system of claim 18, wherein the disposable chamber is a first disposable chamber, and which includes a second disposable chamber, wherein the volume of air delivered is corrected using an average of a temperature in the two disposable chambers.

21. The dialysis system of claim 18, wherein the calculated corrected volume of air delivered to the disposable chamber includes one of (i) a correction factor of a ratio of a temperature of the disposable chamber to a temperature of the reference chamber, and (ii) a correction factor of a ratio of a calibration temperature of the reference chamber to a calibration temperature of the disposable chamber.

22. The dialysis system of claim 18, wherein the pneumatic distribution manifold is contained within a door assembly of the dialysis system.

23. The dialysis system of claim 18, wherein the heater is a first heater, and which includes a second heater and an enclosure including a positive pressure air tank, a negative pressure air tank and the second heater, and wherein the controller is further configured to heat the enclosure and control a temperature of the air tanks with the second heater.

24. The dialysis system of claim 23, wherein the first heater is at least one of a thermocouple and a thermistor mounted to the reference volume chamber.

25. The dialysis system of claim 23, wherein the pneumatic distribution manifold, the enclosure, the air tanks, and the disposable chamber are contained within a door assembly of the dialysis system.

* * * * *